US006316436B1

(12) United States Patent
deSolms et al.

(10) Patent No.: US 6,316,436 B1
(45) Date of Patent: Nov. 13, 2001

(54) INHIBITORS OF PRENYL-PROTEIN TRANSFERASE

(75) Inventors: S. Jane deSolms, Norristown; Anthony W. Shaw, Lansdale, both of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/455,627

(22) Filed: Dec. 7, 1999

Related U.S. Application Data

(60) Provisional application No. 60/111,621, filed on Dec. 8, 1998, now abandoned.

(51) Int. Cl.⁷ .................. A61K 31/55; C07D 267/22; C07D 281/18; C07D 291/00; C07D 487/00
(52) U.S. Cl. ........................... 514/211.1; 540/469
(58) Field of Search ................. 514/211.1; 540/469

(56) References Cited

U.S. PATENT DOCUMENTS

| | | | |
|---|---|---|---|
| 4,060,243 | 11/1977 | Strehlke et al. | 424/273 |
| 4,916,144 | 4/1990 | Strehlke et al. | 514/399 |
| 5,756,528 | 5/1998 | Anthony et al. | 514/399 |
| 5,780,488 | 7/1998 | Bergman et al. | 514/357 |
| 5,780,492 | 7/1998 | Dinsmore et al. | 514/397 |

FOREIGN PATENT DOCUMENTS

| | | |
|---|---|---|
| 0 875 506 A1 | 11/1998 | (EP) . |
| 928788 | 7/1999 | (EP) . |
| WO 97/16443 | 5/1997 | (WO) . |
| WO 97/17070 | 5/1997 | (WO) . |
| WO 97/21701 | 6/1997 | (WO) . |
| WO 97/30992 | 8/1997 | (WO) . |
| WO 97/44350 | 11/1997 | (WO) . |
| WO 98/02436 | 1/1998 | (WO) . |
| WO 98/32741 | 7/1998 | (WO) . |
| WO 98/34921 | 8/1998 | (WO) . |
| WO 98/40383 | 9/1998 | (WO) . |
| WO 98/49157 | 11/1998 | (WO) . |
| WO 99/01434 | 1/1999 | (WO) . |
| WO 99/20611 | 4/1999 | (WO) . |
| WO 99/20612 | 4/1999 | (WO) . |
| WO 99/55725 | 11/1999 | (WO) . |
| WO 00/01382 | 1/2000 | (WO) . |
| WO 00/01701 | 1/2000 | (WO) . |
| WO 00/01702 | 1/2000 | (WO) . |

OTHER PUBLICATIONS

Exp. Opin. Ther. Patents, vol. 9, No. 9, pp. 1263–1280 (1999), by T. M. Williams.
Eur. J. Med. Chem—Chimica Therapeutica, vol. 15, No. 4, (1980), pp. 375–385, by G. Bradley, et al.
Exp. Opin Ther. Patents, vol. 6, No. 12 (1996), pp. 1295–1304, by S. L. Graham, et al.
Exp. Opin. Ther. Patents, vol. 5, No. 12 (1995), pp. 1269–1285, by S. L. Graham.
J. of Biol. Chem., vol. 268, No. 11 (1993), pp. 7617–7620, by J. B. Gibbs, et al.
J. of Biol. Chem., vol. 266, No. 24 (1991), pp. 15575–15578, by J. L. Goldstein, et al.
J. of Biol. Chem., vol. 269, No. 44 (1994), pp. 27705–27714, by G. L. James et al.
J. of Biol. Chem., vol. 270, No. 11 (1995), pp. 6221–6226, by G. L. James, et al.
Nature Medicine, vol. 1, No. 8 (1995), pp. 792–797, by N. E. Kohl, et al.
Science, vol. 260 (1993), pp. 1934–1937, by N. E. Kohl, et al.
Biochemistry, vol. 31 (1992), pp. 3800–3807, by D. L. Pompliano, et al.
Cancer Research, vol. 55 (1995), pp. 5302–5309, by L. Sepp–Lorenzino.
Proc. Natl. Acad. Sci USA, vol. 91 (1994), pp. 9141–9144, by N. E. Kohl, et al.

*Primary Examiner*—Bruck Kifle
(74) *Attorney, Agent, or Firm*—Dianne Brown; Mark R. Daniel

(57) ABSTRACT

The present invention is directed to compounds which inhibit prenyl-protein transferase and particularly, the farnesylation of the oncogene protein Ras. The invention is further directed to chemotherapeutic compositions containing the compounds of this invention and methods for inhibiting farnesyl-protein transferase and the farnesylation of the oncogene protein Ras.

17 Claims, No Drawings

SEQUENCE LISTING

<160> NUMBER OF SEQ ID NOS: 21

<210> SEQ ID NO 1
<211> LENGTH: 4
<212> TYPE: PRT
<213> ORGANISM: Homosapien

<400> SEQUENCE: 1

Cys Val Leu Leu
 1

<210> SEQ ID NO 2
<211> LENGTH: 15
<212> TYPE: PRT
<213> ORGANISM: Homosapien

<400> SEQUENCE: 2

Gly Lys Lys Lys Lys Lys Ser Lys Thr Lys Cys Val Ile Met
 1               5                   10                  15

<210> SEQ ID NO 3
<211> LENGTH: 52
<212> TYPE: DNA
<213> ORGANISM: Artificial Sequence
<220> FEATURE:
<223> OTHER INFORMATION: completely synthesized

<400> SEQUENCE: 3
gagagggaat tcgggccctt cctgcatgct gctgctgctg ctgctgctgg gc            52

<210> SEQ ID NO 4
<211> LENGTH: 41
<212> TYPE: DNA
<213> ORGANISM: Artificial Sequence
<220> FEATURE:
<223> OTHER INFORMATION: completely synthesized

<400> SEQUENCE: 4
gagagagctc gaggttaacc cgggtgcgcg gcgtcggtgg t                        41

<210> SEQ ID NO 5
<211> LENGTH: 42
<212> TYPE: DNA
<213> ORGANISM: Artificial Sequence
<220> FEATURE:
<223> OTHER INFORMATION: completely synthesized

<400> SEQUENCE: 5
gagagagtct agagttaacc cgtggtcccc gcgttgcttc ct                       42

<210> SEQ ID NO 6
<211> LENGTH: 43
<212> TYPE: DNA
<213> ORGANISM: Artificial Sequence
<220> FEATURE:
<223> OTHER INFORMATION: completely synthesized

<400> SEQUENCE: 6
gaagaggaag cttggtaccg ccactgggct gtaggtggtg gct                      43

<210> SEQ ID NO 7
<211> LENGTH: 27
<212> TYPE: DNA
<213> ORGANISM: Artificial Sequence
<220> FEATURE:
<223> OTHER INFORMATION: completely synthesized

<400> SEQUENCE: 7
ggcagagctc gtttagtgaa ccgtcag                                                27

<210> SEQ ID NO 8
<211> LENGTH: 27
<212> TYPE: DNA
<213> ORGANISM: Artificial Sequence
<220> FEATURE:
<223> OTHER INFORMATION: completely synthesized

<400> SEQUENCE: 8
gagagatctc aaggacggtg actgcag                                                27

<210> SEQ ID NO 9
<211> LENGTH: 86
<212> TYPE: DNA
<213> ORGANISM: Artificial Sequence
<220> FEATURE:
<223> OTHER INFORMATION: completely synthesized

<400> SEQUENCE: 9
tctcctcgag gccaccatgg ggagtagcaa gagcaagcct aaggacccca gccagcgccg          60
gatgacagaa tacaagcttg tggtgg                                                86

<210> SEQ ID NO 10
<211> LENGTH: 33
<212> TYPE: DNA
<213> ORGANISM: Artificial Sequence
<220> FEATURE:
<223> OTHER INFORMATION: completely synthesized

<400> SEQUENCE: 10
cacatctaga tcaggacagc acagacttgc agc                                        33

<210> SEQ ID NO 11
<211> LENGTH: 41
<212> TYPE: DNA
<213> ORGANISM: Artificial Sequence
<220> FEATURE:
<223> OTHER INFORMATION: completely synthesized

<400> SEQUENCE: 11
tctcctcgag gccaccatga cagaatacaa gcttgtggtg g                               41

<210> SEQ ID NO 12
<211> LENGTH: 38
<212> TYPE: DNA
<213> ORGANISM: Artificial Sequence
<220> FEATURE:
<223> OTHER INFORMATION: completely synthesized

<400> SEQUENCE: 12
cactctagac tggtgtcaga gcagcacaca cttgcagc                                   38

<210> SEQ ID NO 13
<211> LENGTH: 38
<212> TYPE: DNA
<213> ORGANISM: Artificial Sequence
<220> FEATURE:
<223> OTHER INFORMATION: completely synthesized

<400> SEQUENCE: 13

-continued gagagaattc gccaccatga cggaatataa gctggtgg   38

<210> SEQ ID NO 14
<211> LENGTH: 33
<212> TYPE: DNA
<213> ORGANISM: Artificial Sequence
<220> FEATURE:
<223> OTHER INFORMATION: completely synthesized

<400> SEQUENCE: 14
gagagtcgac gcgtcaggag agcacacact tgc   33

<210> SEQ ID NO 15
<211> LENGTH: 22
<212> TYPE: DNA
<213> ORGANISM: Artificial Sequence
<220> FEATURE:
<223> OTHER INFORMATION: completely synthesized

<400> SEQUENCE: 15
ccgccggcct ggaggagtac ag   22

<210> SEQ ID NO 16
<211> LENGTH: 38
<212> TYPE: DNA
<213> ORGANISM: Artificial Sequence
<220> FEATURE:
<223> OTHER INFORMATION: completely synthesized

<400> SEQUENCE: 16
gagagaattc gccaccatga ctgagtacaa actggtgg   38

<210> SEQ ID NO 17
<211> LENGTH: 32
<212> TYPE: DNA
<213> ORGANISM: Artificial Sequence
<220> FEATURE:
<223> OTHER INFORMATION: completely synthesized

<400> SEQUENCE: 17
gagagtcgac ttgttacatc accacacatg gc   32

<210> SEQ ID NO 18
<211> LENGTH: 21
<212> TYPE: DNA
<213> ORGANISM: Artificial Sequence
<220> FEATURE:
<223> OTHER INFORMATION: completely synthesized

<400> SEQUENCE: 18
gttggagcag ttggtgttgg g   21

<210> SEQ ID NO 19
<211> LENGTH: 38
<212> TYPE: DNA
<213> ORGANISM: Artificial Sequence
<220> FEATURE:
<223> OTHER INFORMATION: completely synthesized

<400> SEQUENCE: 19
gagaggtacc gccaccatga ctgaatataa acttgtgg   38

<210> SEQ ID NO 20
<211> LENGTH: 36
<212> TYPE: DNA
<213> ORGANISM: Artificial Sequence

```
<220> FEATURE:
<223> OTHER INFORMATION: completely synthesized

<400> SEQUENCE: 20
ctctgtcgac gtatttacat aattacacac tttgtc                36

<210> SEQ ID NO 21
<211> LENGTH: 24
<212> TYPE: DNA
<213> ORGANISM: Artificial Sequence
<220> FEATURE:
<223> OTHER INFORMATION: completely synthesized

<400> SEQUENCE: 21
gtagttggag ctgttggcgt aggc                             24
```

INHIBITORS OF PRENYL-PROTEIN TRANSFERASE

The priority of U.S. Provisional Application No. 60/111,621, filed on Dec. 8, 1998, now abandoned, is claimed.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. Such enzymes may be generally termed prenyl-protein transferases. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop compounds that will inhibit a prenyl-protein transferase. It is a further object of this invention to develop chemotherapeutic compositions containing the compounds of this invention and methods for producing the compounds of this invention.

SUMMARY OF THE INVENTION

The present invention comprises macrocyclic compounds which inhibit a prenyl-protein transferase. Further contained in this invention are chemotherapeutic compositions containing these prenyl-protein transferase inhibitors and methods for their production.

The compounds of this invention are illustrated by the formula A:

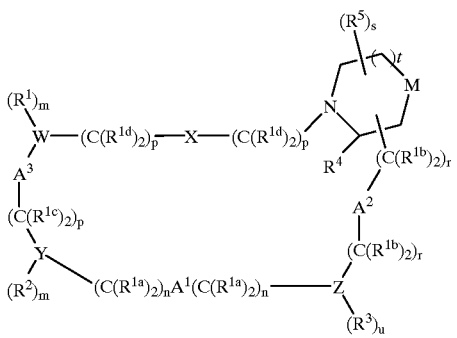

DETAILED DESCRIPTION OF THE INVENTION

The compounds of this invention are useful in the inhibition of prenyl-protein transferase and the prenylation of the oncogene protein Ras. In a first embodiment of this invention, the inhibitors of a prenyl-protein transferase are illustrated by the formula A:

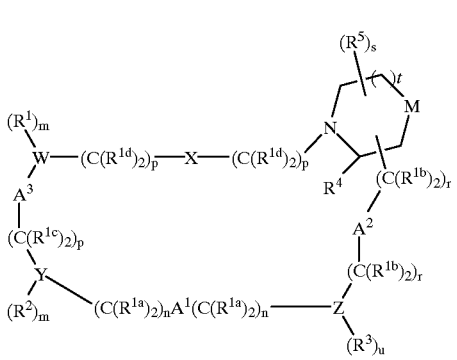

wherein:
$R^{1a}$, $R^{1b}$, $R^{1c}$ and $R^{1d}$ are independently selected from:
   a) hydrogen,
   b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)_2$—, or $N_3$;
   c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;
$R^1$ is selected from:
   a) H,
   b) unsubstituted or substituted $C_1$–$C_6$ alkyl,
   c) unsubstituted or substituted aryl,
   d) unsubstituted or substituted heterocycle,
   e) —($C_1$–$C_6$ alkyl)$N(R^8)_2$,
   f) —$R^8C(O)R^8$,
   g) —($C_1$–$C_6$ alkyl)$OR^8$,
   h) —$N(R^8)_2$,
   i) —$OR^8$,
   j) —$R^8NHC(O)R^8$,
   k) —$R^8C(O)N(R^8)_2$,
   l) $CF_3$,
   m) halo,
   n) —$C(O)OR^8$,
   o) $C_2$–$C_6$ alkynyl,
   p) $C_2$–$C_6$ alkenyl,
   q) perfluoroalkyl,
   r) $N_3$,
   s) $NO_2$,
   t) CN,
   u) $R^9S(O)_q$—

$R^2$ is selected from:
   a) hydrogen,
   b) CN,
   c) $NO_2$,
   d) halogen,
   e) aryl, unsubstituted or substituted,
   f) heteroaryl, unsubstituted or substituted,
   g) $C_1$–$C_6$ alkyl, unsubstituted or substituted,
   h) $OR^8$,
   i) $N_3$,
   j) $R^9S(O)_q$,
   k) $R^8HC$=$CH$—, and
   l) $R^8C$≡$C$—;

$R^3$ is selected from:
   a) H,
   b) CN,
   c) $NO_2$,
   d) halogen,
   e) $C_1$–$C_6$ alkyl, unsubstituted or substituted,
   f) $OR^8$,
   g) aryl, unsubstituted or substituted,
   h) heteroaryl, unsubstituted or substituted, and
   i) $CF_3$;

$R^4$ is selected from:
   a) H,
   b) =O, or
   c) =S;

$R^5$ is selected from:
   a) H,
   b) CN,
   c) $NO_2$,
   d) halogen,
   e) $C_1$–$C_6$ alkyl, unsubstituted or substituted,
   f) $N_3$,
   g) $R^9S(O)_q$,
   h) —HC=$CH_2$,
   i) HC≡C—,
   j) aryl, unsubstituted or substituted,
   k) heterocycle, unsubstituted or substituted,
   l) $CF_3O$—,
   m) $CF_3CH_2O$—,
   n) $C_3$–$C_{10}$ cycloalkyl,
   o) $CF_3$,
   p) —($C_1$–$C_6$ alkyl)$N(R^8)_2$,
   q) —($C_1$–$C_6$ alkyl)$OR^8$,
   r) $OR^8$,
   s) $N(R^8)_2$,
   t) —$C(O)(C_1$–$C_6$ alkyl), and
   u) —($C_1$–$C_6$ alkyl)$C(O)R^8$;

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

R⁹ is independently selected from unsubstituted or substituted $C_1$–$C_6$ alkyl, unsubstituted or substituted benzyl and unsubstituted or substituted aryl;

$A^1$ and $A^2$ are independently selected from:
a) a bond,
   b) —HC=CH—,
   c) —C≡C—,
   d) O,
   e) $S(O)_q$,
   f) OC(O),
   g) C(O),
   h) C(O)O, and
   i) $NR^8$;

$A^3$ is selected from a bond, —C(=O),

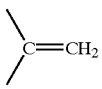

and $C_3$–$C_6$ cycloalkyl;

M is selected from $CH_2$, NH, O or S;
provided that if t is 1, then M is not NH;

W is selected from:
a) heterocycle, and
b) aryl;
   provided that W is not piperazinyl, 2-oxopiperazinyl or diketo piperazinyl;

X is selected from: a bond, —C(=O)— or —$S(O)_q$—;

Y is selected from:
a) aryl, and
b) heterocycle;
   provided that Y is not piperazinyl, 2-oxopiperazinyl or diketo piperazinyl;

Z is selected from:
a) aryl,
b) heterocycle,
c) $C_3$–$C_6$ cycloalkyl, and
d) a bond;
   provided that Z is not piperazinyl, 2-oxopiperazinyl or diketo piperazinyl;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
t is 1, 2 or 3;
u is 0, 1, 2, 3 or 4, provided that when Z is a bond, u is 0;

or a pharmaceutically acceptable salt, an optical isomer or stereoisomer thereof.

In another embodiment, the compounds of the instant invention are illustrated by formula A:

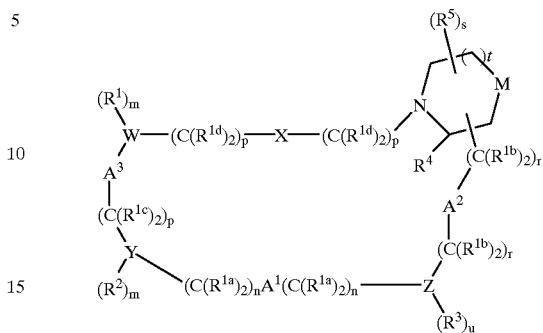

A wherein:
$R^{1a}$, $R^{1b}$, $R^{1c}$ and $R^{1d}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)_2$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)$N(R^8)_2$,
f) —$R^8C(O)R^8$,
g) —($C_1$–$C_6$ alkyl)$OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC=CH$—, and
l) $R^8C≡C$—;

R³ is selected from:
  a) H,
  b) CN,
  c) NO₂,
  d) halogen,
  e) $C_1$–$C_6$ alkyl, unsubstituted or substituted,
  f) OR⁸,
  g) aryl, unsubstituted or substituted,
  h) heteroaryl, unsubstituted or substituted, and
  i) CF₃;
R⁴ is selected from:
  a) H,
  b) =O, or
  c) =S;
R⁵ is selected from:
  a) H,
  b) CN,
  c) NO₂,
  d) halogen,
  e) $C_1$–$C_6$ alkyl, unsubstituted or substituted,
  f) N₃,
  g) $R^9S(O)_q$,
  h) —HC=CH₂,
  i) HC≡C—,
  j) aryl, unsubstituted or substituted,
  k) heterocycle, unsubstituted or substituted,
  l) CF₃O—,
  m) CF₃CH₂O—,
  n) $C_3$–$C_{10}$ cycloalkyl,
  o) CF₃,
  p) —($C_1$–$C_6$ alkyl)N(R⁸)₂,
  q) —($C_1$–$C_6$ alkyl)OR⁸,
  r) OR⁸,
  s) N(R⁸)₂,
  t) —C(O)($C_1$–$C_6$ alkyl), and
  u) —($C_1$–$C_6$ alkyl)C(O)R⁸;
R⁸ is independently selected from hydrogen, unsubstituted or substituted $C_1$–$C_6$ alkyl, unsubstituted or substituted benzyl, unsubstituted or substituted heterocycle and unsubstituted or substituted aryl;
R⁹ is independently selected from unsubstituted or substituted $C_1$–$C_6$ alkyl, unsubstituted or substituted benzyl and unsubstituted or substituted aryl;
A¹ and A² are independently selected from:
  a) a bond,
  b) O,
  c) $S(O)_q$,
  d) OC(O),
  e) C(O),
  f) C(O)O, and
  g) NR⁸;
A³ is selected from a bond, —C(=O),

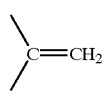

and $C_3$–$C_6$ cycloalkyl;
M is selected from CH₂, NH, O or S;
  provided that if t is 1, then M is not NH;
W is selected from:
  a) heteroaryl, and
  b) aryl;
X is selected from: a bond, —C(=O)— or —S(O)_q—;

Y is selected from:
  a) aryl, and
  b) heteroaryl;
Z is selected from:
  a) aryl,
  b) heteroaryl,
  c) $C_3$–$C_6$ cycloalkyl, and
  d) a bond;
m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
t is 1, 2 or 3;
u is 0, 1, 2, 3 or 4, provided that when Z is a bond, u is 0;
or a pharmaceutically acceptable salt, an optical isomer or stereoisomer thereof.

In another embodiment, the compounds of the instant invention are illustrated by formula B:

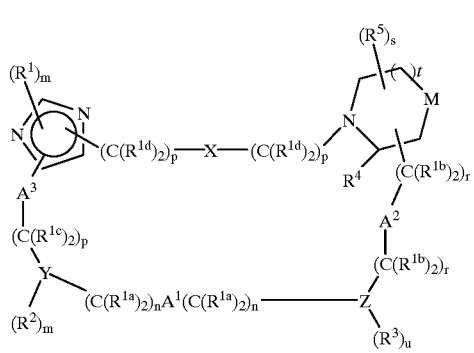

wherein:
  $R^{1a}$, $R^{1b}$, $R^{1c}$ and $R^{1d}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, R⁸O—, $R^9S(O)_q$—, CN, NO₂, R⁸C(O)—, R⁸OC(O)—, N(R⁸)₂, (R⁸)₂NC(O)—, C(O)N(R⁸)₂—, or N₃;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, R⁸O—, $R^9S(O)_q$—, CN, R⁸C(O)—, R⁸OC(O)—, N(R⁸)₂, N₃, or R⁸C(O)O—;
R¹ is selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)N(R⁸)₂,
  f) —R⁸C(O)R⁸,
  g) —($C_1$–$C_6$ alkyl)OR⁸,
  h) —N(R⁸)₂,
  i) —OR⁸,
  j) —R⁸NHC(O)R⁸,
  k) —R⁸C(O)N(R⁸)₂,
  l) CF₃,
  m) halo,
  n) —C(O)OR⁸, o) C$_2$–C$_6$ alkynyl,
p) C$_2$–C$_6$ alkenyl,
q) perfluoroalkyl,
r) N$_3$,
s) NO$_2$,
t) CN,
u) R$^9$S(O)$_q$—

R$^2$ is selected from:
a) hydrogen,
b) CN,
c) NO$_2$,
d) halogen,
e) aryl, unsubstituted or substituted,
f) heteroaryl, unsubstituted or substituted,
g) C$_1$–C$_6$ alkyl, unsubstituted or substituted,
h) OR$^8$,
i) N$_3$,
j) R$^8$S(O)$_q$,
k) R$^8$HC=CH—, and
l) R$^8$C≡C—;

R$^3$ is selected from:
a) H,
b) CN,
c) NO$_2$,
d) halogen,
e) C$_1$–C$_6$ alkyl, unsubstituted or substituted,
f) OR$^8$,
g) aryl, unsubstituted or substituted,
h) heteroaryl, unsubstituted or substituted, and
i) CF$_3$;

R$^4$ is selected from:
a) H,
b) =O, or
c) =S;

R$^5$ is selected from:
a) H,
b) CN,
c) NO$_2$,
d) halogen,
e) C$_1$–C$_6$ alkyl, unsubstituted or substituted,
f) N$_3$,
g) R$^9$S(O)$_q$,
h) —HC=CH$_2$,
i) HC≡C—,
j) aryl, unsubstituted or substituted,
k) heterocycle, unsubstituted or substituted,
l) CF$_3$O—,
m) CF$_3$CH$_2$O—,
n) C$_3$–C$_{10}$ cycloalkyl,
o) CF$_3$,
p) —(C$_1$–C$_6$ alkyl)N(R$^8$)$_2$,
q) —(C$_1$–C$_6$ alkyl)OR$^8$,
r) OR$^8$,
s) N(R$^8$)$_2$,
t) —C(O)(C$_1$–C$_6$ alkyl), and
u) —(C$_1$–C$_6$ alkyl)C(O)R$^8$;

R$^8$ is independently selected from hydrogen, unsubstituted or substituted C$_1$–C$_6$ alkyl or substituted benzyl, unsubstituted or substituted heterocycle and unsubstituted or substituted aryl;

R$^9$ is independently selected from unsubstituted or substituted C$_1$–C$_6$ alkyl, unsubstituted or substituted benzyl and unsubstituted or substituted aryl;

A$^1$ and A$^2$ are independently selected from:
a) a bond,
b) O,
c) S(O)$_q$,
d) OC(O),
e) C(O),
f) C(O)O, and
g) NR$^8$;

A$^3$ is selected from a bond, —C(=O),

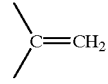

and C$_3$–C$_6$ cycloalkyl;

M is selected from CH$_2$, NH, O or S;
provided that if t is 1, then M is not NH;

X is selected from: a bond, —C(=O)— or —S(O)$_q$—;

Y is selected from:
a) aryl, and
b) heteroaryl;

Z is selected from:
a) aryl,
b) heteroaryl, and
c) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
t is 1, 2 or 3;
u is 0, 1, 2, 3 or 4, provided that when Z is a bond, u is 0;

or a pharmaceutically acceptable salt, an optical isomer or stereoisomer thereof.

In further embodiment, the compound of the instant invention are illustrated by formula C:

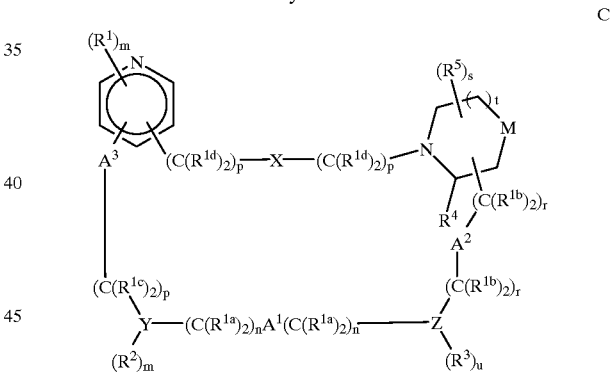

C wherein:

R$^{1a}$, R$^{1b}$, R$^{1c}$ and R$^{1d}$ are independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^8$O—, R$^9$S(O)$_q$—, CN, NO$_2$, R$^8$C(O)—, R$^8$OC(O)—, N(R$^8$)$_2$, (R$^8$)$_2$NC(O)—, C(O)N(R$^8$)$_2$—, or N$_3$;
c) C$_1$–C$_6$ alkyl, unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^8$O—, R$^9$S(O)$_q$—, CN, R$^8$C(O)—, R$^8$OC(O)—, N(R$^8$)$_2$, N$_3$, or R$^8$C(O)O—;

R$^1$ is selected from:
a) H,
b) unsubstituted or substituted C$_1$–C$_6$ alkyl,
c) unsubstituted or substituted aryl,
d) unsubstituted or substituted heterocycle,
e) —(C$_1$–C$_6$ alkyl)N(R$^8$)$_2$,
f) —R$^8$C(O)R$^8$, g) —(C$_1$–C$_6$ alkyl)OR$^8$,
h) —N(R$^8$)$_2$,
i) —OR$^8$,
j) —R$^8$NHC(O)R$^8$,
k) —R$^8$C(O)N(R$^8$)$_2$,
l) CF$_3$,
m) halo,
n) —C(O)OR$^8$,
o) C$_2$–C$_6$ alkynyl,
p) C$_2$–C$_6$ alkenyl,
q) perfluoroalkyl,
r) N$_3$,
s) NO$_2$,
t) CN,
u) R$^9$S(O)$_q$—

R$^2$ is selected from:
a) hydrogen,
b) CN,
c) NO$_2$,
d) halogen,
e) aryl, unsubstituted or substituted,
f) heteroaryl, unsubstituted or substituted,
g) C$_1$–C$_6$ alkyl, unsubstituted or substituted,
h) OR$^8$,
i) N$_3$,
j) R$^9$S(O)$_q$,
k) R$^8$HC=CH—, and
l) R$^8$C≡C—;

R$^3$ is selected from:
a) H,
b) CN,
c) NO$_2$,
d) halogen,
e) C$_1$–C$_6$ alkyl, unsubstituted or substituted,
f) OR$^8$,
g) aryl, unsubstituted or substituted,
h) heteroaryl, unsubstituted or substituted, and
i) CF$_3$;

R$^4$ is selected from:
a) H,
b) =O, or
c) =S;

R$^5$ is selected from:
a) H,
b) CN,
c) NO$_2$,
d) halogen,
e) C$_1$–C$_6$ alkyl, unsubstituted or substituted,
f) N$_3$,
g) R$^9$S(O)$_q$,
h) —HC=CH$_2$,
i) HC≡C—,
j) aryl, unsubstituted or substituted,
k) heterocycle, unsubstituted or substituted,
l) CF$_3$O—,
m) CF$_3$CH$_2$O—,
n) C$_3$–C$_{10}$ cycloalkyl,
o) CF$_3$,
p) —(C$_1$–C$_6$ alkyl)N(R$^8$)$_2$,
q) —(C$_1$–C$_6$ alkyl)OR$^8$,
r) OR$^8$,
S) N(R$^8$)$_2$,
t) —C(O)(C$_1$–C$_6$ alkyl), and
u) —(C$_1$–C$_6$ alkyl)C(O)R$^8$;

R$^8$ is independently selected from hydrogen, unsubstituted or substituted C$_1$–C$_6$ alkyl, unsubstituted or substituted benzyl, unsubstituted or substituted heterocycle and unsubstituted or substituted aryl;

R$^9$ is independently selected from unsubstituted or substituted C$_1$–C$_6$ alkyl, unsubstituted or substituted benzyl and unsubstituted or substituted aryl;

A$^1$ and A$^2$ are independently selected from:
a) a bond,
b) O,
c) S(O)$_q$,
d) OC(O),
e) C(O),
f) C(O)O, and
g) NR$^8$;

A$^3$ is selected from a bond, —C(=O), $$\diagup_{\diagdown}C=CH_2$$

and C$_3$–C$_6$ cycloalkyl;

M is selected from CH$_2$, NH, O or S;
provided that if t is 1, then M is not NH;

X is selected from: a bond, —C(=O)— or —S(O)$_q$—;

Y is selected from:
a) aryl, and
b) heteroaryl;

Z is selected from:
a) aryl,
b) heteroaryl, and
c) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
t is 1, 2 or 3;
u is 0, 1, 2, 3 or 4, provided when Z is a bond, u is 0;

or a pharmaceutically acceptable salt, an optical isomer or stereoisomer thereof.

In a further embodiment, the compounds of the instant invention are illustrated by formula D:

wherein:

R$^{1a}$, R$^{1b}$, R$^{1c}$ and R$^{1d}$ are independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, R$^8$O—, R$^9$S(O)$_q$—, CN, NO$_2$, R$^8$C(O)—, R$^8$OC(O)—, N(R$^8$)$_2$, (R$^8$)$_2$NC(O)—, C(O)N(R$^8$)$_2$—, or N$_3$;
c) C$_1$–C$_6$ alkyl, unsubstituted or substituted by unsubstituted or substituted aryl, unsubstituted or substituted heterocycle, C$_3$–C$_{10}$ cycloalkyl, C$_2$–C$_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —$(C_1$–$C_6$ alkyl)$N(R^8)_2$,
f) —$R^8C(O)R^8$,
g) —$(C_1$–$C_6$ alkyl)$OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC=CH$—, and
l) $R^8C\equiv C$—;

$R^3$ is selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is selected from:
a) H,
b) =O, or
c) =S;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —$HC=CH_2$,
i) $HC\equiv C$—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$, p) —$(C_3$–$C_6$ alkyl)$N(R^8)_2$,
q) —$(C_1$–$C_6$ alkyl)$OR^8$,
r) $OR^8$,
s) $N(R^8)_2$,
t) —$C(O)(C_1$–$C_6$ alkyl), and
u) —$(C_1$–$C_6$ alkyl)$C(O)R^8$;

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$A^1$ and $A^2$ are independently selected from:
a) a bond,
b) O,
c) $S(O)_q$,
d) OC(O),
e) C(O),
f) C(O)O, and
g) $NR^8$;

$A^3$ is selected from a bond, —C(=O),

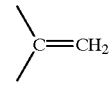

and $C_3$–$C_6$ cycloalkyl;

X is selected from: a bond, —C(=O)— or —$S(O)_q$—;

Z is selected from:
a) aryl,
b) heteroaryl, and
c) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
t is 1, 2 or 3;
u is 0, 1, 2, 3 or 4, provided that when Z is a bond, u is 0;

or a pharmaceutically acceptable salt, an optical isomer or stereoisomer thereof.

In a further embodiment, the compounds of the instant invention are illustrated by formula E:

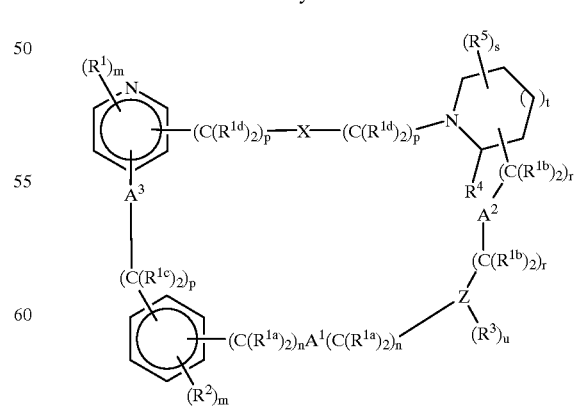

wherein:
$R^{1a}$, $R^{1b}$, $R^{1c}$ and $R^{1d}$ are independently selected from:
a) hydrogen, b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)_2$—, or $N_3$;

c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —$(C_1$–$C_6$ alkyl$)N(R^8)_2$,
f) —$R^8C(O)R^8$,
g) —$(C_1$–$C_6$ alkyl$)OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC$=$CH$—, and
l) $R^8C$≡$C$—;

$R^3$ is selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is selected from:
a) H,
b) =O, or
c) =S;

$R^5$ is selected from:
a) H,
b) CN,
c) $NO_2$,
d) halogen,
e) $C_1$–$C_6$ alkyl, unsubstituted or substituted,
f) $N_3$, g) $R^9S(O)_q$,
h) —HC=$CH_2$,
i) HC≡C—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —$(C_1$–$C_6$ alkyl$)N(R^8)_2$,
q) —$(C_1$–$C_6$ alkyl$)OR^8$,
r) $OR^8$,
s) $N(R^8)_2$,
t) —$C(O)(C_1$–$C_6$ alkyl), and
u) —$(C_1$–$C_6$ alkyl$)C(O)R^8$;

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$A^1$ and $A^2$ are independently selected from:
a) a bond,
b) O,
c) $S(O)_q$,
d) OC(O),
e) C(O),
f) C(O)O, and
g) $NR^8$;

$A^3$ is selected from a bond, —C(=O),

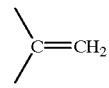

and $C_3$–$C_6$ cycloalkyl;

X is selected from: a bond, —C(=O)— or —$S(O)_q$—;

Z is selected from:
a) aryl,
b) heteroaryl, and
c) a bond;

m is 0, 1, 2, 3 or 4;

n is 0, 1, 2, 3 or 4;

p is 0, 1, 2, 3 or 4;

q is 0, 1 or 2;

r is 0, 1, 2, 3, or 4;

s is 0, 1, 2, 3 or 4;

t is 1, 2 or 3;

u is 0, 1, 2, 3 or 4, provided that when Z is a bond, u is 0;

or a pharmaceutically acceptable salt, an optical isomer or stereoisomer thereof.

In a further embodiment, the compounds of the instant invention are illustrated by formula F:

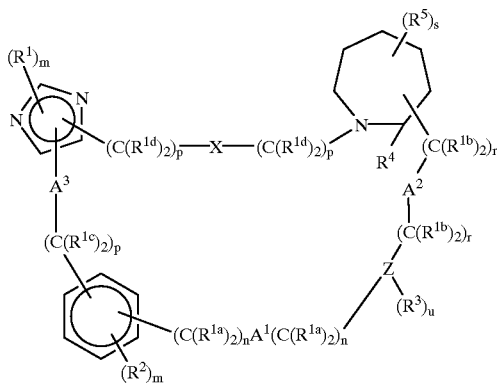

wherein:

$R^{1a}$, $R^{1b}$, $R^{1c}$ and $R^{1d}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)_2$—, or $N_3$;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)$N(R^8)_2$,
  f) —$R^8C(O)R^8$,
  g) —($C_1$–$C_6$ alkyl)$OR^8$,
  h) —$N(R^8)_2$,
  i) —$OR^8$,
  j) —$R^8NHC(O)R^8$,
  k) —$R^8C(O)N(R^8)_2$,
  l) $CF_3$,
  m) halo,
  n) —$C(O)OR^8$,
  o) $C_2$–$C_6$ alkynyl,
  p) $C_2$–$C_6$ alkenyl,
  q) perfluoroalkyl,
  r) $N_3$,
  s) $NO_2$,
  t) CN,
  u) $R^9S(O)_q$—

$R^2$ is selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $OR^8$,
  i) $N_3$,
  j) $R^9S(O)_q$,
  k) $R^8HC=CH$—, and
  l) $R^8C\equiv C$—;

$R^3$ is selected from:
  a) H,
  b) CN,
  c) $NO_2$,
  d) halogen,
  e) $C_1$–$C_6$ alkyl, unsubstituted or substituted,
  f) $OR^8$,
  g) aryl, unsubstituted or substituted,
  h) heteroaryl, unsubstituted or substituted, and
  i) $CF_3$;

$R^4$ is selected from:
  a) H,
  b) =O, or
  c) =S;

$R^5$ is selected from:
  a) H,
  b) CN,
  c) $NO_2$,
  d) halogen,
  e) $C_1$–$C_6$ alkyl, unsubstituted or substituted,
  f) $N_3$,
  g) $R^9S(O)_q$,
  h) —$HC=CH_2$,
  i) $HC\equiv C$—,
  j) aryl, unsubstituted or substituted,
  k) heterocycle, unsubstituted or substituted,
  l) $CF_3O$—,
  m) $CF_3CH_2O$—,
  n) $C_3$–$C_{10}$ cycloalkyl,
  o) $CF_3$,
  p) —($C_1$–$C_6$ alkyl)$N(R^8)_2$,
  q) —($C_1$–$C_6$ alkyl)$OR^8$,
  r) $OR^8$,
  s) $N(R^8)_2$,
  t) —$C(O)(C_1$–$C_6$ alkyl), and
  u) —($C_1$–$C_6$ alkyl)$C(O)R^8$;

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$A^1$ and $A^2$ are independently selected from:
  a) a bond,
  b) O,
  c) $S(O)_q$,
  d) OC(O),
  e) C(O),
  f) C(O)O, and
  g) $NR^8$;

$A^3$ is selected from a bond, —C(=O),

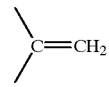

and $C_3$–$C_6$ cycloalkyl;

X is selected from: a bond, —C(=O)— or —$S(O)_q$—;

Z is selected from:
  a) aryl,
  b) heteroaryl, and
  c) a bond;

m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
u is 0, 1, 2, 3 or 4, provided that when Z is a bond, u is 0;

or a pharmaceutically acceptable salt, an optical isomer or stereoisomer thereof.

In a further embodiment, the compounds of the instant invention are illustrated by formula G:

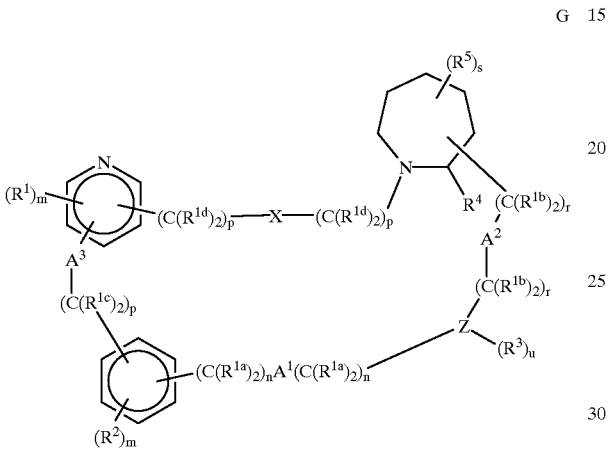

G wherein:
$R^{1a}$, $R^{1b}$, $R^{1c}$ and $R^{1d}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)_2$—, or $N_3$;
c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
a) H,
b) unsubstituted or substituted $C_1$–$C_6$ alkyl,
c) unsubstituted or substituted aryl,
d) unsubstituted or substituted heterocycle,
e) —($C_1$–$C_6$ alkyl)$N(R^8)_2$,
f) —$R^8C(O)R^8$,
g) —($C_1$–$C_6$ alkyl)$OR^8$,
h) —$N(R^8)_2$,
i) —$OR^8$,
j) —$R^8NHC(O)R^8$,
k) —$R^8C(O)N(R^8)_2$,
l) $CF_3$,
m) halo,
n) —$C(O)OR^8$,
o) $C_2$–$C_6$ alkynyl,
p) $C_2$–$C_6$ alkenyl,
q) perfluoroalkyl,
r) $N_3$,
s) $NO_2$,
t) CN,
u) $R^9S(O)_q$—

$R^2$ is selected from:
a) hydrogen,
b) CN,
c) $NO_2$,
d) halogen,
e) aryl, unsubstituted or substituted,
f) heteroaryl, unsubstituted or substituted,
g) $C_1$–$C_6$ alkyl, unsubstituted or substituted,
h) $OR^8$,
i) $N_3$,
j) $R^9S(O)_q$,
k) $R^8HC$=CH—, and
l) $R^8C$≡C—;

$R^3$ is selected from:
a) H,
b) CN,
c) $NO_2$,
d) halogen,
e) $C_1$–$C_6$ alkyl, unsubstituted or substituted,
f) $OR^8$,
g) aryl, unsubstituted or substituted,
h) heteroaryl, unsubstituted or substituted, and
i) $CF_3$;

$R^4$ is selected from:
a) H,
b) =O, or
c) =S;

$R^5$ is selected from:
a) H,
b) CN,
c) $NO_2$,
d) halogen,
e) $C_1$–$C_6$ alkyl, unsubstituted or substituted,
f) $N_3$,
g) $R^9S(O)_q$,
h) —HC=$CH_2$,
i) HC≡C—,
j) aryl, unsubstituted or substituted,
k) heterocycle, unsubstituted or substituted,
l) $CF_3O$—,
m) $CF_3CH_2O$—,
n) $C_3$–$C_{10}$ cycloalkyl,
o) $CF_3$,
p) —($C_1$–$C_6$ alkyl)$N(R^8)_2$,
q) —($C_1$–$C_6$ alkyl)$OR^8$,
r) $OR^8$,
s) $N(R^8)_2$,
t) —$C(O)(C_1$–$C_6$ alkyl), and
u) —($C_1$–$C_6$ alkyl)$C(O)R^8$;

$R^8$ is independently selected from hydrogen, unsubstituted or substituted $C_1$–$C_6$ alkyl, unsubstituted or substituted benzyl, unsubstituted or substituted heterocycle and unsubstituted or substituted aryl;

$R^9$ is independently selected from unsubstituted or substituted $C_1$–$C_6$ alkyl, unsubstituted or substituted benzyl and unsubstituted or substituted aryl;

$A^1$ and $A^2$ are independently selected from:
a) a bond,
b) O,
c) $S(O)_q$,
d) OC(O),
f) C(O)O, and
g) $NR^8$;

A³ is selected from a bond, —C(=O),

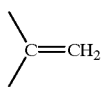

and C₃–C₆ cycloalkyl;
X is selected from: a bond, —C(=O)— or —S(O)$_q$—;
Z is selected from:
  a) aryl,
  b) heteroaryl, and
  c) a bond;
m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
u is 0, 1, 2, 3 or 4, provided that when Z is a bond, u is 0;
or a pharmaceutically acceptable salt, an optical isomer or stereoisomer thereof.

Specific examples of the compound of the instant invention are:

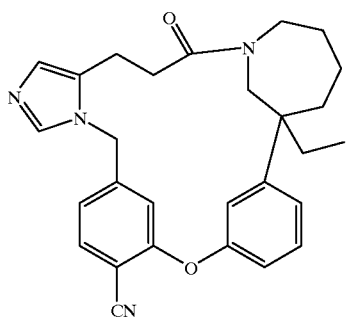

(±) 5H-17-Ethyl-17,22-methano-18,19,20,21,23,24-hexahydro-23-oxo-6,10:12,16-dimetheno-25H-imidazo[3,4-h]-[1,11,16]oxadiazacyclodocosane-9-carbonitrile or a pharmaceutically acceptable salt, an optical isomer or stereoisomer thereof.

The compounds of the present invention may have asymmetric centers and occur as racemates, racemic mixtures, and as individual diastereomers, with all possible isomers, including optical isomers, being included in the present invention. When any variable, substituent or term (e.g. aryl, heterocycle, $R^{1a}$, $R^2$, n, p, etc.) occurs more than one time in a formula or generic structure, its definition at each occurrence is independent of the definition at every other occurrence. Also, combinations of substituents/or variables are permissible only if such combinations result in stable compounds.

As used herein, "alkyl" is intended to include both branched and straight-chain saturated aliphatic hydrocarbon groups having 1 to 6 carbon atoms, unless otherwise specified; "alkoxy" represents an alkyl group having 1 to 4 carbon atoms, unless otherwise indicated, attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, indanonyl, biphenyl, tetralinyl, tetralonyl, fluorenonyl, phenanthryl, anthryl or acenaphthyl.

As used herein, "aralkyl" is intended to mean an aryl moiety, as defined above, attached through a $C_1$–$C_6$ alkyl linker, where alkyl is defined above. Examples of aralkyls inlcude, but are not limited to, benzyl, naphthylmethyl and phenylpropyl.

As used herein, "heteroaralkyl" is intended to mean a heteroaryl moiety, as defined below, attached through a $C_1$–$C_6$ alkyl linker, where alkyl is defined above. Examples of heteroaralkyls include, but are not limited to, 2-pyridylmethyl, 2-morpholinylethyl, 2-imidazolylethyl, 2-quinolinylmethyl, 2-imidazolylmethyl and the like.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, benzopyrazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, 2-oxopyridyl, 2-oxoquinolinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, the terms "substituted $C_1$–$C_6$ alkyl" and "substituted $C_1$–$C_6$ alkoxy" are intended to include the branch or straight-chain alkyl group of the specified number of carbon atoms, wherein the carbon atoms may be substituted with F, Cl, Br, $CF_3$, $N_3$, $NO_2$, $NH_2$, oxo, —OH, —O($C_1$–$C_6$ alkyl), S(O)$_{0-2}$, ($C_1$–$C_6$ alkyl)S(O)$_{0-2}$—, ($C_1$–$C_6$ alkyl)S(O)$_{0-2}$($C_1$–$C_6$ alkyl)—, $C_3$–$C_{10}$ cycloalkyl, $C_2$–$C_6$ alkenyl, $C_2$–$C_6$ alkynyl, —C(O)NH, ($C_1$–$C_6$ alkyl)C(O)NH—, $H_2N$—C(NH)—, ($C_1$–$C_6$ alkyl)C(O)—, —O($C_1$–$C_6$ alkyl)CF$_3$, (C$_1$–C$_6$ alkyl)OC(O)—, (C$_1$–C$_6$ alkyl)O(C$_1$–C$_6$ alkyl)—, (C$_1$–C$_6$ alkyl)C(O)$_2$(C$_1$–C$_6$ alkyl)—, (C$_1$–C$_6$ alkyl)OC(O)NH—, aryl, benzyl, heterocycle, aralkyl, heteroaralkyl, halo-aryl, halo-benzyl, halo-heterocycle, cyano-aryl, cyano-benzyl and cyano-heterocycle.

As used herein, the terms "substituted aryl", "substituted heteroaryl", "substituted benzyl" and "substituted heterocycle" are intended to include the cyclic group containing from 1 to 3 substitutents in addition to the point of attachment to the rest of the compound. Such substitutents are preferably selected from the group which includes but is not limited to F, Cl, Br, CF$_3$, NH$_2$, N(C$_1$–C$_6$ alkyl)$_2$, NO$_2$, CN, N$_3$, C$_1$–C$_{20}$ alkyl, C$_1$–C$_6$ alkoxy, —OH, —O(C$_1$–C$_6$ alkyl), S(O)$_{0-2}$, (C$_1$–C$_6$ alkyl)S(O)$_{0-2}$—, (C$_1$–C$_6$ alkyl)S(O)O$_{0-2}$ (C$_1$–C$_6$ alkyl)—, (C$_1$–C$_6$ alkyl)C(O)NH—, H$_2$N—C(NH)—, (C$_1$–C$_6$ alkyl)C(O)—, (C$_1$–C$_6$ alkyl)OC(O)—, (C$_1$–C$_6$ alkyl)O(C$_1$–C$_6$ alkyl)—, (C$_1$–C$_6$ alkyl)C(O)$_2$(C$_1$–C$_6$ alkyl)—, (C$_1$–C$_6$ alkyl)OC(O)NH—, aryl, aralkyl, heteroaryl, heteroaralkyl, halo-aryl, halo-aralkyl, halo-heterocycle, halo-heteroaralkyl, cyano-aryl, cyano-aralkyl, cyano-heterocycle and cyano-heteroaralkyl.

Examples of the moiety

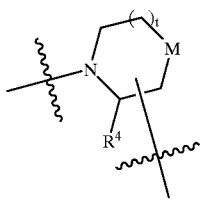

include, but are not limited to,

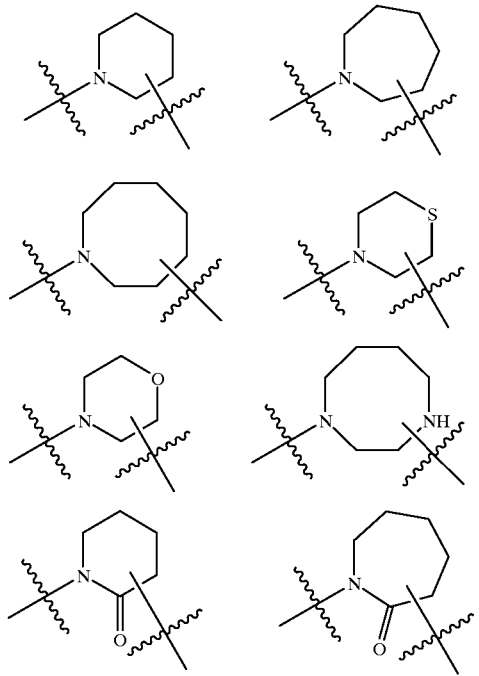

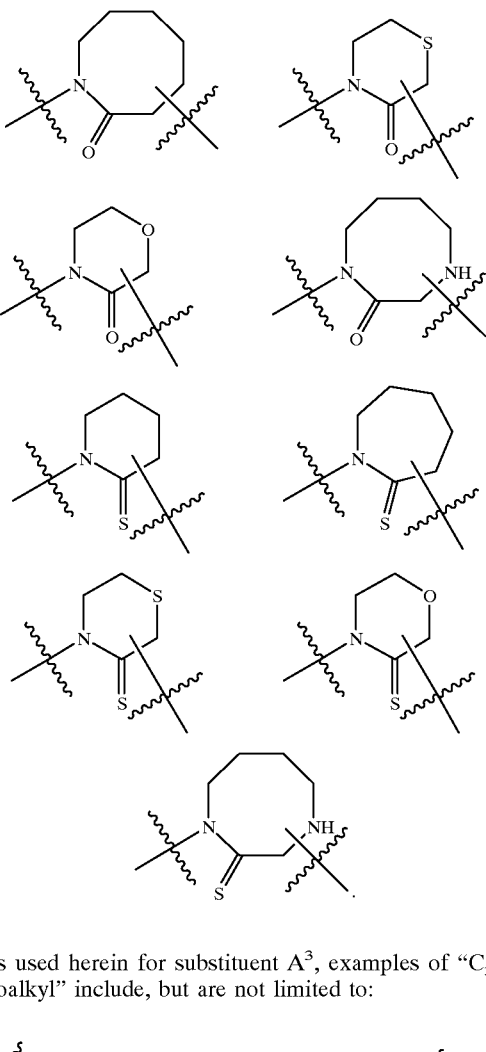

As used herein for substituent A$^3$, examples of "C$_3$–C$_6$ cycloalkyl" include, but are not limited to:

Lines drawn into the ring systems from substituents (such as from R$^2$, R$^3$, R$^5$ etc.) indicate that the indicated bond may be attached to any of the substitutable ring carbon atoms or heteroatom.

Preferably, R$^{1a}$, R$^{1b}$, R$^{1c}$ and R$^{1d}$ are independently selected from: hydrogen, unsubstituted or substituted C$_1$–C$_6$ alkyl, unsubstituted or substituted aryl, unsubstituted or substituted heterocycle, —OR$^8$, or —N(R$^8$)$_2$.

Preferably, R$^1$ is independently selected from H, halo, unsubstituted or substituted C$_1$–C$_6$ alkyl, —OR$^8$, —N(R$^8$)$_2$, —(C$_1$–C$_6$ alkyl)N(R$^8$)$_2$, unsubstituted or substituted aryl, or unsubstituted or substituted heterocycle.

Preferably, $R^2$ is independently selected from H, $OR^8$, CN, unsubstituted or substituted aryl or halogen. Most preferably, $R^2$ is CN.

Preferably, $R^3$ is independently selected from hydrogen, halogen, CN, $NO_2$, and unsubstituted or substituted $C_1$–$C_6$ alkyl.

Preferably, $R^4$ is selected from H or =O.

Preferably, $R^5$ is independently selected from hydrogen, halogen, unsubstituted or substituted $C_1$–$C_6$ alkyl, unsubstituted or substituted aryl, unsubstituted or substituted heterocycle, —($C_1$–$C_6$ alkyl)$N(R^8)_2$ or —($C_1$–$C_6$ alkyl)$OR^8$.

Preferably, $A^1$ and $A^2$ are independently selected from: a bond, O, —$NR^8$ and $S(O)_q$. Most preferably, $A^1$ is O or S and $A^2$ is a bond.

Preferably, $A^3$ is selected from a bond, C(=O) or $C_3$–$C_6$ cycloalkyl.

Preferably, W is a heteroaryl. Most preferably, W is imidazolyl or pyridyl.

Preferably, Y is selected from phenyl or pyridyl. Most preferably, Y is phenyl.

Preferably, Z is selected from aryl, a bond or a heteroaryl. More preferably, Z is an aryl. Most preferably, Z is phenyl.

Preferably, m, n, p, q, r, s and u are independently 0, 1, or 2.

Preferably, t is 1 or 2. Most preferably, t is 2.

Preferably, the moiety

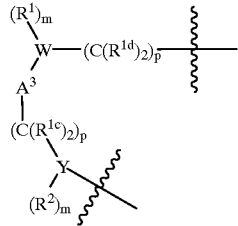

is selected from:

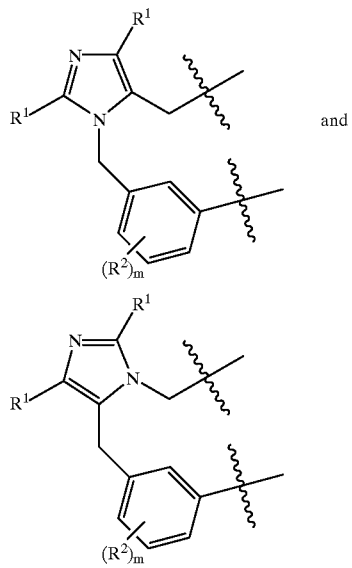

It is intended that the definition of any substituent or variable (e.g., $R^{1a}$, $R^5$, n, m, etc.) at a particular location in a molecule be independent of its definitions elsewhere in that molecule. Thus, —$N(R^8)_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations which may be used in the description of the chemistry and in the Examples that follow include:

| | |
|---|---|
| $Ac_2O$ | Acetic anhydride; |
| AIBN | 2,2'-azobisisobutyronitrile |
| Boc | t-Butoxycarbonyl; |
| CBz | Carbobenzyloxy; |
| DBU | 1,8-diazabicyclo[5,4,0]undec-7-ene; |
| DMAP | 4-Dimethylaminopyridine; |
| DME | 1,2-Dimethoxyethane; |
| DMF | Dimethylformamide; |
| DMSO | Methyl sulfoxide; |
| DTT | Dithiothreitol; |
| EDC | 1-(3-dimethylaminopropyl)-3-ethyl-carbodiimide-hydrochloride; |
| EDTA | Ethylenediaminetetraacetic acid; |
| $Et_3N$ | Triethylamine; |
| EtOAc | Ethyl acetate; |
| EtOH | Ethanol; |
| FAB | Fast atom bombardment; |
| HEPES | 4-(2-hydroxyethyl)-l-piperazineethanesulfonic acid; |
| HOBT | l-Hydroxybenzotnazole hydrate; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MeOH | methanol |
| MsCl | Methanesulfonyl chloride; |
| NaHMDS | Sodium bis(trimethylsilyl)amide; |
| NBS | N-bromosuccinimide; |
| PMSF | αtoluenesulfonyl chloride; |
| Py or pyr | Pyridine; |
| RPLC | Reverse Phase Liquid Chromatography |
| TFA | Trifluoroacetic acid; |
| THF | Tetrahydrofuran. |

Synopsis of Schemes

Schemes 1 to 11 describe the synthesis of compounds of formulae A through G. The starting materials can be obtained from commercial sources or they can be obtained using standard transformations from commerically available materials.

In Scheme 1 the imidazole propionate I, prepared by hydrogenation of urocanic acid and subsequent protection, was quaternized with an aralkyl halide, followed by methanolysis to remove the trityl group and hydrolysis of the ester to give acid II.

Schemes 2 and 2A illustrate the procedures which may be used to prepare intermediate compounds of formulae IIIa/IIIc and V/Va. Other procedures are described by G. Bradley et al. in Eur. J. Med. Chem. (1980) 15, [4], 375. The commercially available lactam was protected by silylation, then deprotonated with lithium tetramethylpiperidide and reacted with the benzyne generated from an ortho halo anisole to give compound III/IIIb. Reduction of III/IIIb provided the amine IV/IVa. Both III/IIIb and IV/IVa are demethylated to give phenols IIa/IIIc and V/Va.

Scheme 3 describes the formation of the macrocycle VII. The acid II and the amine V were coupled under standard coupling conditions to give compound VI. Treatment of compound VI with cesium carbonate in a solvent such as DMF or DMSO provided the macrocycle VII. This cyclization reaction depends on the presence of an electronic withdrawing moiety (such as nitro, cyano, and the like) either ortho or para to the fluorine atom.

In Scheme 4 imidazole acetic acid is used as a starting material to prepare compound IX following a procedure similar to that described in Scheme 1. Scheme 5 shows the synthesis of macrocycle XI. Scheme 6 exemplifies the use of a reductive alkylation to prepare intermediate XIII which is cyclized to macrocycle XIV. In Scheme 7 the penultimate intermediate is prepared by alkylation of protected amide IIIb. Subsequent treatment with cesium carbonate removes the mesylate and forms the macrocycle XV.

Scheme 8 illustrates a method to prepare a pyridine-containing intermediates XIX and XX, which can be used in the procedures described hereinabove to give a pyridine-containing macrocycle.

Scheme 9 illustrates the synthetic strategy that is employed when the $R^2$ substitutent is not an electronic withdrawing moiety either ortho or para to the fluorine atom. In the absence of the electronic withdrawing moiety, the intramolecular cyclization can be accomplished via an Ullmann reaction. Thus, the benzylimidazolylaldehyde is coupled with the phenol V. Coupling under standard Ullmann conditions provided compound XIV of the instant invention.

Schemes 10 and 11 illustrate routes for preparing macrocycles XXII and XXIV, which are linked through a benzyl-substituted lactam.

SCHEME 1

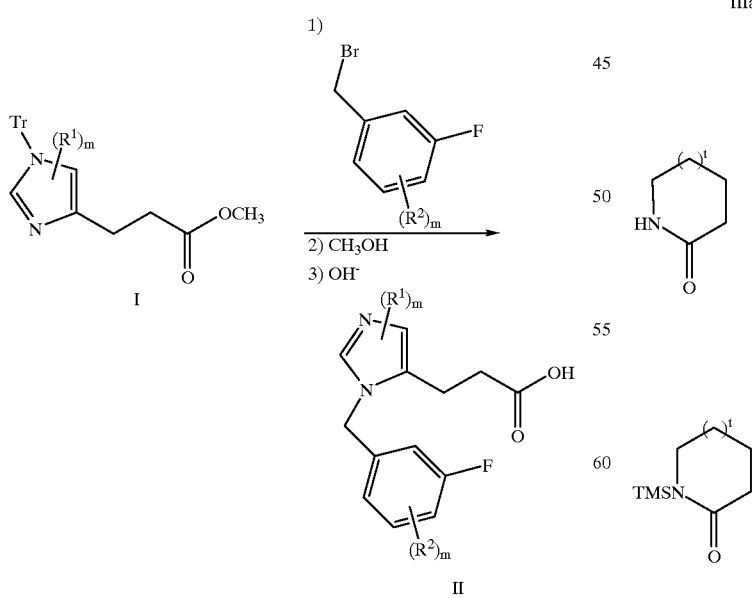

SCHEME 2

SCHEME 2A

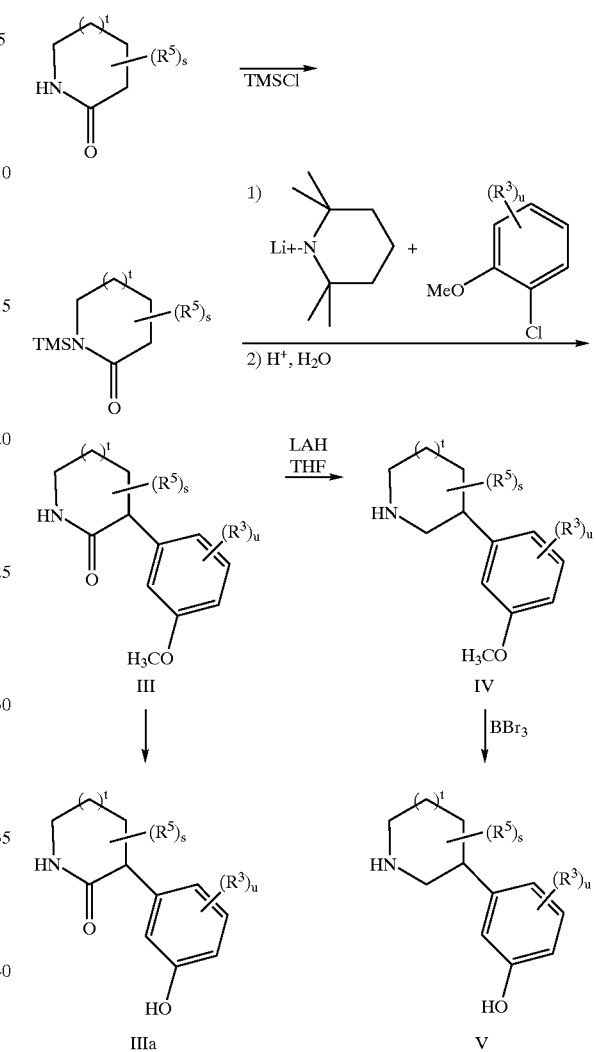

-continued
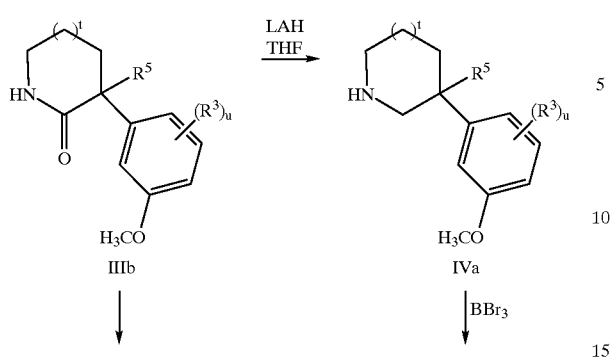
IIIb
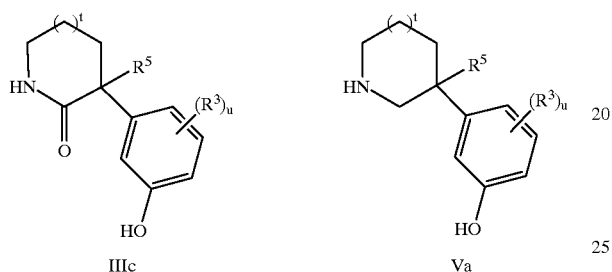
IIIc
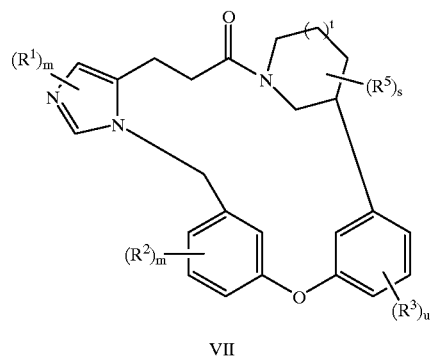
VII
SCHEME 3
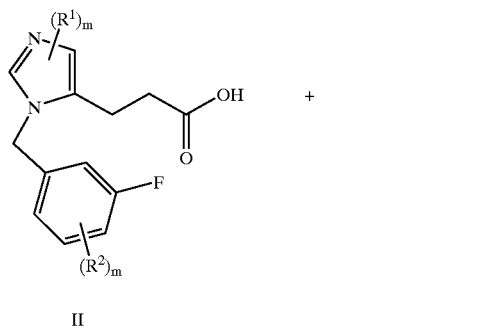
II
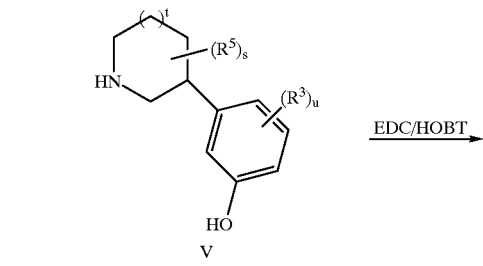
V
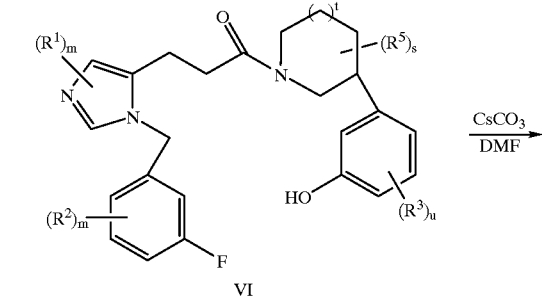
VI
-continued
SCHEME 4
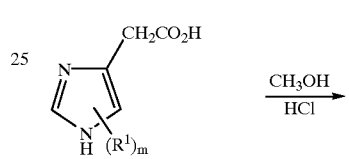
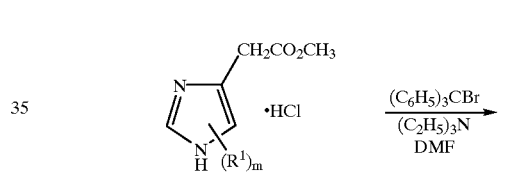
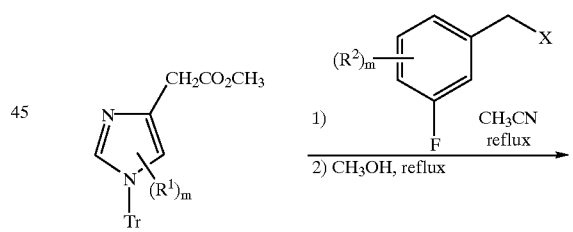
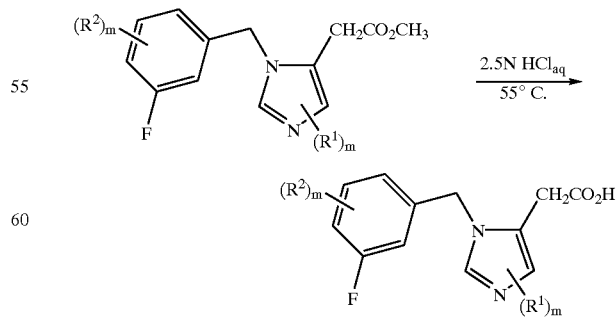
IX SCHEME 5
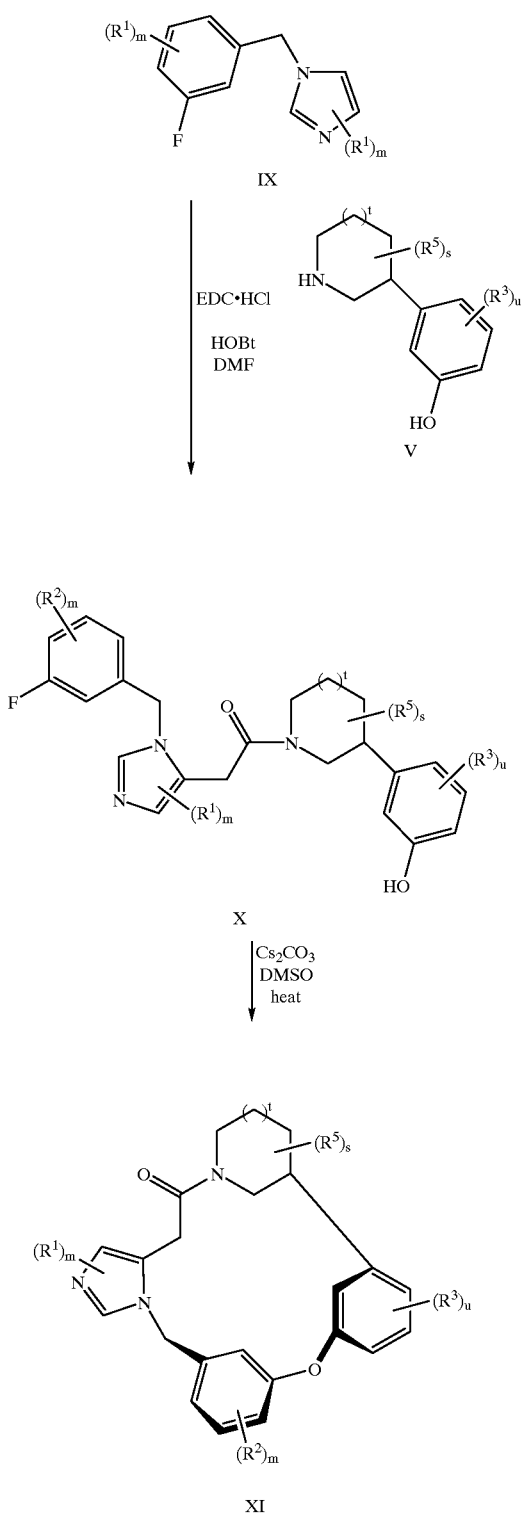
SCHEME 6
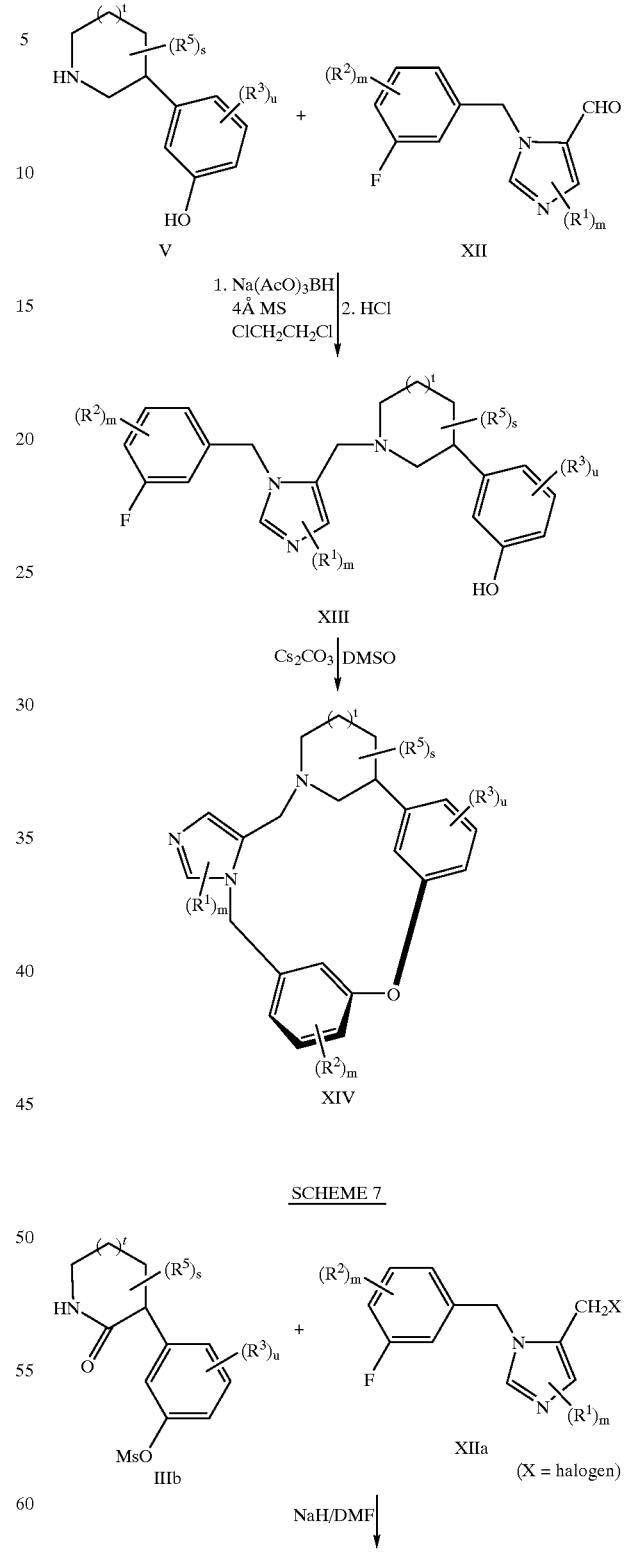
SCHEME 7
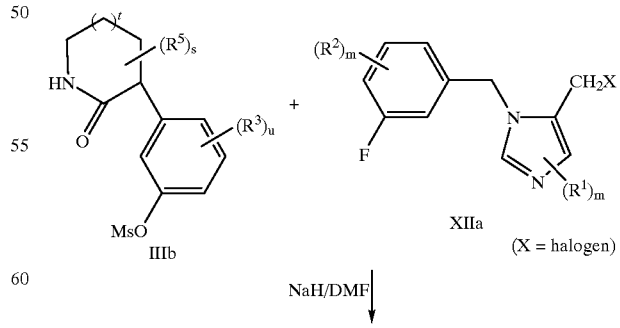

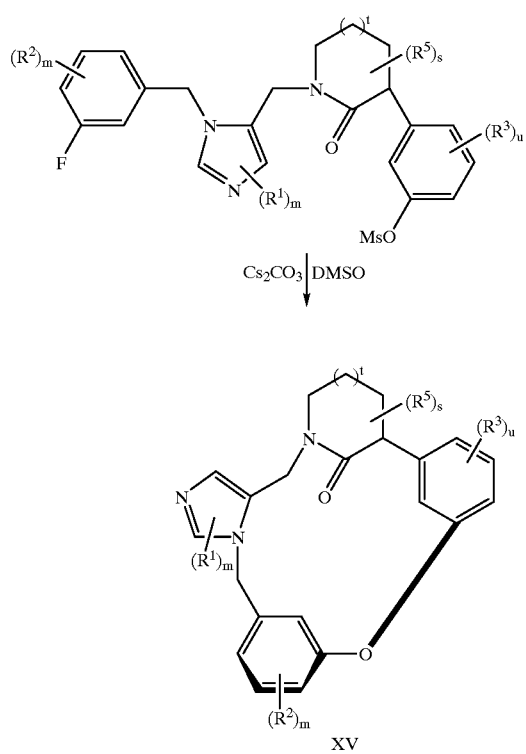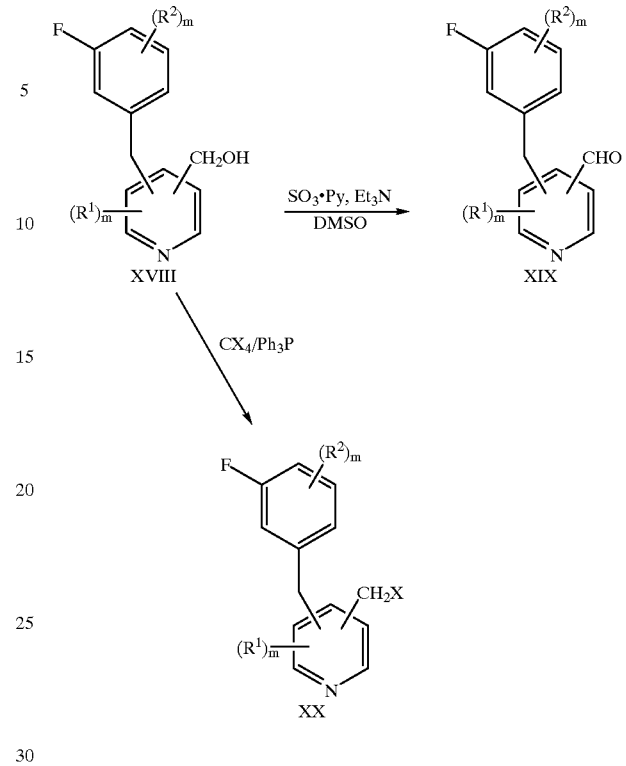
SCHEME 8
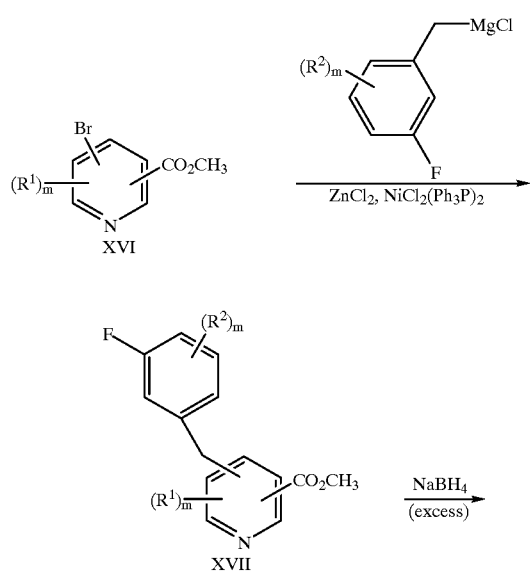
SCHEME 9

SCHEME 10

SCHEME 11

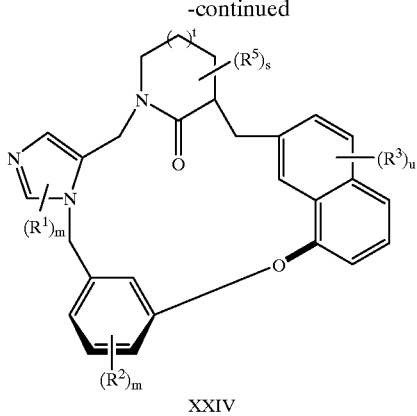

XXIV

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 2, is at least 100 times greater than the in vitro activity of the same compound against geranylgeranyl-protein transferase-type I in the assay described in Example 3. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:
  b) an $IC_{50}$ (a measure of in vitro inhibitory activity) for inhibition of the prenylation of newly synthesized K-Ras protein more than about 100-fold higher than the $IC_{50}$ for the inhibition of the farnesylation of hDJ protein.

When measuring such $IC_{50}$s the assays described in Examples 7 and 8 may be utilized.

It is also preferred that the selective inhibitor of farnesyl-protein transferase is further characterized by:
  c) an $IC_{50}$ (a measurement of in vitro inhibitory activity) for inhibition of K4B-Ras dependent activation of MAP kinases in cells at least 100-fold greater than the $IC_{50}$ for inhibition of the farnesylation of the protein hDJ in cells.

It is also preferred that the selective inhibitor of farnesyl-protein transferase is further characterized by:
  d) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells.

When measuring Ras dependent activation of MAP kinases in cells the assays described in Example 6 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Example 6, it is preferred that the dual inhibitor compound has an in vitro inhibitory activity ($IC_{50}$) that is less than about 12 μM against K4B-Ras dependent activation of MAP kinases in cells.

The Class II prenyl-protein transferase inhibitor may also be characterized by:
  a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and
  b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:
  a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and
  b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:
  a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and
  b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 6.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, ab1, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55: 4575–4580 (1995)). Such anti-angiogenes is properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science,* 256:1331–1333 (1992).

The compounds of the instant invention are also useful in the prevention of restenosis after percutaneous transluminal coronary angioplasty by inhibiting neointimal formation (C. Indolfi et al. *Nature medicine,* 1:541–545(1995).

The instant compounds may also be useful in the treatment and prevention of polycystic kidney disease (D. L. Schaffner et al. *American Journal of Pathology,* 142:1051–1060 (1993) and B. Cowley, Jr. et al. *FASEB Journal,* 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of the instant invention may also be useful in the prevention and treatment of endometriosis, uterine fibroids, dysfunctional uterine bleeding and endometrial hyperplasia.

In such methods of prevention and treatment, the prenyl-protein transferase inhibitor may also be co-administered with other well known therapeutic agents that are selected for their particular usefulness against the condition that is being treated. For example, the prenyl-protein transferase inhibitor may be useful in further combination with drugs known to supress the activity of the ovaries and slow the growth of the endometrial tissue. Such drugs include but are not limited to oral contraceptives, progestins, danazol and GnRH (gonadotropin-releasing hormone) agonists.

Administration of the prenyl-protein transferase inhibitor may also be combined with surgical treatment of endometriosis (such as surgical removal of misplaced endometrial tissue) where appropriate.

The instant compounds may also be useful as inhibitors of corneal inflammation. These compounds may improve the treatment of corneal opacity which results from cauterization-induced corneal inflammation. The instant compounds may also be useful in reducing corneal edema and neovascularization. (K. Sonoda et al., *Invest. Ophthalmol. Vis. Sci.,* 1998, vol. 39, p 2245–2251).

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

As used herein, the term "composition" is intended to encompass a product comprising the specified ingredients in the specific amounts, as well as any product which results, directly or indirectly, from combination of the specific ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula A may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant farnesyl-protein transferase inhibitors and an antineoplastic agent. It is also understood that such a combination of antineoplastic agent and inhibitor of farnesyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of farnesyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with farnesyl pyrophosphate competitive inhibitors of the activity of farnesyl-protein transferase or in combination with a compound which has Raf antagonist activity. The instant compounds may also be co-administered with compounds that are selective inhibitors of geranylgeranyl protein transferase.

In particular, if the compound of the instant invention is a selective inhibitor of farnesyl-protein transferase, co-administration with a compound(s) that is a selective inhibitor of geranylgeranyl protein transferase may provide an improved therapeutic effect.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the α1β1, α2β1, α5β1, α6β1 and α6β4 integrins. The term also refers to antagonists of any combination of αvβ3 integrin, αvβ5 integrin, αβ1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

The instant compounds may also be useful in combination with an inhibitor of 3-hydroxy-3-methylglutaryl-CoA reductase (HMG-CoA reductase) for the treatment of cancer. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938; 4,294,926; 4,319,039), simvastatin (ZOCOR®; see U.S. Pat. Nos. 4,444,784; 4,820,850; 4,916,239), pravastatin (PRAVACHOL®; see U.S. Pat. Nos. 4,346,227; 4,537,859; 4,410,629; 5,030,447 and 5,180,589), fluvastatin (LESCOL®; see U.S. Pat. Nos. 5,354,772; 4,911,165; 4,929,437; 5,189,164; 5,118,853; 5,290,946; 5,356,896), atorvastatin (LIPITOR®; see U.S. Pat. Nos. 5,273,995; 4,681,893; 5,489,691; 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (Feb. 5, 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

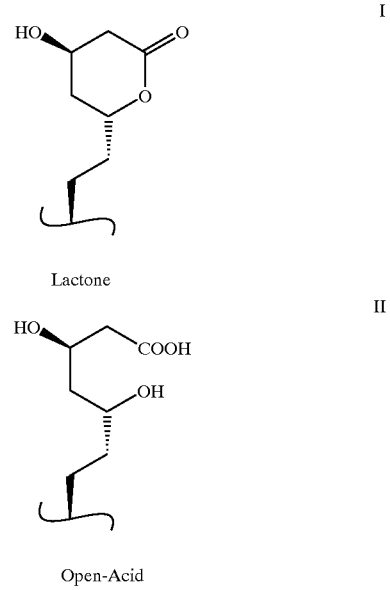

Lactone

Open-Acid

In HMG-CoA reductase inhibitor's where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described above and the other pharmaceutically active agent(s) within its approved dosage range. Combinations of the instant invention may alternatively be used sequentially with known pharmaceutically acceptable agent(s) when a multiple combination formulation is inappropriate.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of (±) 5H-17-Ethyl-17,22-methano-18,19,20,21, 23,24-hexahydro-23-oxo-6,10:12,16-dimetheno-25H-imidazo[3,4-h]-[1,11,16]oxadiazacyclodocosane-9-carbonitrile Step A Preparation of 4-Bromo-3-fluorobenzoic Acid 4-Bromo-3-fluorotoluene (40.0 g, 0.212 mol) was heated at 90° C. in $H_2O$ (200 mL)-pyridine (200 mL) with mechanical stirring under Ar. Potassium permanganate ($KMnO_4$) (67 g, 0.424 mol) was added portionwise over 3 h. After 4 h, an HPLC of a filtered sample indicated 50% conversion to the acid. An additional 30 g of $KMnO_4$ was added and heating continued overnight. HPLC indicated 81% conversion. Further $KMnO_4$ was added portionwise with reaction monitoring by HPLC until >95% conversion was obtained. The reaction mixture was filtered through Celite, the filter pad washed with $H_2O$, aq NaOH and EtOH. The filtrate was concentrated to a small volume, then partitioned between 3N NaOH solution and diethyl ether. The aqueous basic layer was separated, cooled in an ice-$H_2O$ bath and acidified slowly with 6N HCl solution to precipitate the white solid product. This was collected by suction filtration and dried at 40° C. in a vacuum oven overnight to give the title compound. mp 190–192° C.

$^1$H NMR ($CDCl_3$) δ7.83 (dd, 1H, J=2, 9 Hz), 7.78 (dd, 1H, J=2, 8 Hz), 7.67–7.71 (m, 1H).

Step B

Preparation of 4-bromo-3-fluorobenzyl Alcohol

4-Bromo-3-fluorobenzoic acid, as described above, (40.8 g, 0.187 mol) was dissolved in THF (250 ml) with magnetic stirring under Ar in an ice-$H_2O$ bath. The cloudy solution was treated dropwise with borane-THF complex (1 M) (374 mL, 0.374 mol) over a 1 h period maintaining the internal temperature at <10° C. The reaction mixture was left to warm to ambient temperature overnight, then cooled in an ice-$H_2O$ bath and treated dropwise with $H_2O$ (150 mL). The THF was removed on a rotary evaporator, and the residue partitioned between EtOAc and $H_2O$. The aqueous layer was extracted with EtOAc (3×100 mL), the organic layers combined, washed with brine, and dried ($Na_2SO_4$), filtered, and concentrated to give the title compound as an oil which solidified on standing.

$^1$H NMR ($CDCl_3$) δ7.52 (t, 1H, J=8 Hz), 7.16 (d, 1H, J=9 Hz), 7.02 (d, 1H, J=8 Hz), 4.67 (s, 2H), 1.47 (br s, 1H).

Step C
Preparation of 2-fluoro-4-hydroxymethylbenzonitrile

4-Bromo-3-fluorobenzyl alcohol, as described in Step B above, (20 g, 0.097 mol) was dissolved in DMF (100 mL) then placed under high vacuum for 15 min. The solution was then purged with Ar for 15 min. While purging continued, zinc cyanide (8 g, 0.068 mol) and the catalyst, $Pd[(PPh_2)]_4$, (5.63 g, 0.0049 mol) were added. The reaction mixture was heated at 95° C. under Ar for 18 h, then cooled to ambient temperature and added to $H_2O$. The mixture was extracted with EtOAc, then washed with 1M HCl, $H_2O$, brine, and dried ($Na_2SO_4$). Filtration and concentration to dryness gave the title compound as a white solid after chromatography (silica gel, hexane: EtOAc, 6.5:3.5).

$^1$H NMR ($CDCl_3$) δ7.61 (t, 1H, J=8 Hz), 7.23–7.29 (m, 2H), 4.80 (d, 2H, J=6 Hz), 1.93 (t, 1H, J=6 Hz).

Step D
Preparation of 4-Bromomethyl-2-fluoro-benzonitrile

N-Bromosuccinimide (6.6 g, 0.037 mol) was dissolved in $CH_2Cl_2$ (150 mL), cooled to 0° C. and treated with dimethylsulfide (3.27 mL, 0.0446 mol). The solution was cooled to −20° C. then treated dropwise with a solution of 2-fluoro-4-hydroxymethylbenzonitrile, as described in Step C above, (3.74 g, 0.0248 mol) in $CH_2Cl_2$ (30 mL). After the addition, the reaction mixture was stirred at 0° C. for 2 h then left to warm to ambient temperature overnight. The reaction mixture was added to ice/$H_2O$, extracted with EtOAc, the organic layer separated, washed with brine and dried ($MgSO_4$). Filtration and concentration to dryness gave the title compound which was purified after chromatography (silica gel, 5–10% EtOAc/hexane).

$^1$H NMR ($CDCl_3$) δ7.61 (dd, 1H, J=8, 8 Hz), 7.26–7.30 (m, 2H), 4.45 (s, 2H).

Step E
Preparation of 3-[3-(4-cyano-3-fluoro-benzyl)-3H-imidazol-4-yl]-propionic Acid 1-Trityl-imidazole-4-propionic acid methyl ester (2.15 g, 5.42 mmol) and 4-bromomethyl-2-fluoro-benzonitrile, as described above in Step D, (1.16 g, 5.42 mmol) were dissolved in EtOAc (20 mL) and heated at 60° C. for 3 h. The precipitated solid was filtered off, and the filtrate was concentrated to 10 mL then heating at 60° C. was continued overnight. The precipitate was collected and combined with the first solid and heated at reflux in $CH_3OH$ (20 mL) for 5 h. The reaction mixture was concentrated to dryness and triturated with hexane to remove triphenylmethane. The residue was dissolved in THF (10 mL)-$H_2O$ (5 mL), treated with 1 N NaOH (5 mL) and stirred at ambient temperature for 16 h. The reaction mixture was neutralized with 1N HCl (5 mL), concentrated to remove the THF, then lyophilized to give the title compound.

Step F
Preparation of 1-trimethylsilanyl-azepan-2-one

Caprolactam, which is commercially available, (10.0 g, 88.0 mmol), $Et_3N$ (14.8 mL, 106 mmol) and chlorotrimethylsilane (13.5 mL, 106 mmol) were dissolved in toluene (60 mL) and refluxed under Ar for 3 h. The reaction was filtered and concentrated to give the title compound.

Step G
Preparation of 3-(3-methoxy-phenyl)-azepan-2-one

To 1.6 M n-BuLi in hexane (31.3 mL, 50 mmol) at 0° C. was added a solution of 2,2,6,6-tetramethyl piperidine (8.43 mL, 50 mmol) in anhydrous THF (100 mL) over 5 min. 1-Trimethylsilanyl-azepan-2-one (as described in Step F above) (9.26 g, 50 mmol) in anhydrous THF (20 mL) was added. After stirring the reaction mixture for 10 min a further portion of 1.6M n-BuLi in hexane (31.3 mL, 50 mmol) was added, the mixture stirred for 10 min, and 2-chloroanisole (6.34 mL, 50 mmol) was added. After stirring for 30 min under Ar, the reaction was quenched with $H_2O$, stirred for 30 min, concentrated in vacuo, diluted with EtOAc, washed with 5N HCl (100 mL) and brine. The organic layer was dried ($MgSO_4$), concentrated and purified using $SiO_2$ chromatography (0.5% MeOH/$CH_2Cl_2$) to give the title compound.

Step H
Preparation of 3-ethyl-3-(3-methoxy-phenyl)-azepan-2-one

To 1.6 M n-BuLi in hexane (31.3 mL, 50 mmol) at 0° C. was added a solution of 2,2,6,6-tetramethyl piperidine (8.43 mL, 50 mmol) in anhydrous THF (100 mL) over 5 min. 1-Trimethylsilanyl-azepan-2-one (as described in Step F above) (9.26 g, 50 mmol) in anhydrous THF (20 mL) was added. After stirring the reaction mixture for 10 min, a further portion of 1.6M n-BuLi in hexane (31.3 mL, 50 mmol) was added, the mixture stirred for 10 min, and 2-chloroanisole (6.34 mL, 50 mmol) was added. After stirring for 30 min under Ar, ethyl iodide (3.90 mL, 48.7 mmol) was added, the reaction mixture was stirred for 30 min, quenched with $H_2O$, concentrated in vacuo, diluted with EtOAc, and washed with 5N HCl (100 mL) and brine. The organic layer was dried ($MgSO_4$), concentrated and purified using $SiO_2$ chromatography (10–15% EtOAc/$CH_2Cl_2$) to give the title compound Step I
Preparation of 3-ethyl-3-(3-methoxy-phenyl)-azepane 3-Ethyl-3-(3-methoxy-phenyl)-azepan-2-one (as described in Step H above) (1.05 g, 4.24 mmol) in anhydrous THF (4.2 mL) was added to a solution of $LiAlH_4$ (0.193 g, 5.09 mmol) in anhydrous THF (4.2 mL) and refluxed for 24 h. The solution was cooled, quenched with $H_2O$ (0.18 mL), 15% NaOH (0.18 mL), $H_2O$ (0.54 mL), filtered and concentrated. The residue was purified using reverse phase chromatography (95/5-5/95 $H_2O$/$CH_3CN$ with 0.1% TFA, flow =65 mL/min) and converted to its free base using saturated $NaHCO_3$ solution, extracted with $CH_2Cl_2$ (3×) and dried ($MgSO_4$) to give the title compound.

Step J
Preparation of 3-(3-ethyl-azepan-3-yl)-phenol

A 1M solution of $BBr_3$ (2.56 mL, 2.56 mmol) in $CH_2Cl_2$ was added to 3-ethyl-3-(3-methoxy-phenyl)-azepane (as described in Step I above) (0.300 g, 0.1.28 mmol) dissolved in anhydrous $CH_2Cl_2$ (10 mL) at −78° C. After 20 h of stirring at room temperature, the reaction was quenched with sat. $NaHCO_3$ solution, extracted with $CH_2Cl_2$ (3×), dried ($MgSO_4$) and concentrated to give the title compound.

Step K
Preparation of 4-(5-{3-[3-ethyl-3-(3-hydroxy-phenyl)-azepan-1-yl]-3-oxo-propyl}-imidazol-1-ylmethyl)-2-fluoro-benzonitrile 3-[3-(4-Cyano-3-fluoro-benzyl)-3H-imidazol-4-yl]-propionic acid, as described above in Step E, (0.56 g, 0.78 mmol) and 3-(3-ethyl-azepan-3-yl)-phenol, as described above in Step J, (0.182 g, 0.78 mmol), HOBT (0.126 g, 0.936 mmol), EDC (0.179 g, 0.936 mmol) and N-methylmorpholine (0.257 mL, 2.34 mmol) were dissolved in DMF (15 mL) and stirred at ambient temperature for 18 h. The DMF was removed in vacuo and the residue was partitioned between EtOAc and saturated aqueous $NaHCO_3$ solution. The organic layer was washed with $H_2O$, brine, dried ($MgSO_4$), filtered, and concentrated to give the title compound.

Step L
Preparation of (±) 5H-17-Ethyl-17,22-methano-18,19,20,21,23,24-hexahydro-23-oxo-6,10:12,16-dimetheno-25H-imidazo[3,4-h]-[1,11,16]oxadiazacyclodocosane-9-carbonitrile 4-(5-{3-[3-ethyl-3-(3-hydroxy-phenyl)-azepan-1-yl]-3-oxo-propyl}-imidazol-1-ylmethyl)-2-fluoro-benzonitrile, as described above in Step K, (0.10 g, 0.21 mmol) and cesium carbonate (0.172 g, 0.526 mmol) were combined in DMF (4.2 mL) and heated at 55° C. for 18 h. The DMF was removed in vacuo and the residue was dissolved in $CH_3OH$ and purified by RP LC on a Waters PrepPak column eluting with 0.1%TFA/$H_2O$: 0.1%TFA/$CH_3CN$, 95:5 to 5:95 gradient. Product fractions were combined, concentrated, then basified with aqueous saturated $NaHCO_3$ solution, extracted with $CH_2Cl_2$, the organic layer separated, dried ($MgSO_4$), and concentrated to give the title compound.

HR MS (M+1): theoretical: 455.2431; measured: 455.2441.

Preparation of enantiomers A and B of (±) 5H-17-Ethyl-17,22-methano-18,19,20,21,23,24-hexahydro-23-oxo-6,10:12,16-dimetheno-25H-imidazo [3,4-h]-[1,11,16] oxadiazacyclodocosane-9-carbonitrile The crude product described in Step L was separated by LC on a Chiracel OD column eluting with 2-propanol:hexane, 65:35 with 0.1% diethylamine.

Concentration to Dryness Gave Enantiomer A

FAB mass spectrum m/e 455 (m+1).

Analysis calculated for $C_{28}H_{30}N_4O_2 \cdot 0.35\ H_2O \cdot 0.30\ CH_2Cl_2$: C, 69.88; H, 6.49; N, 11.52; Found: C, 69.86; H, 6.46; N, 11.38.

and Enantiomer B

FAB mass spectrum m/e 455 (m+1).

Analysis calculated for $C_{28}H_{30}N_4O_2 \cdot 0.10\ H_2O \cdot 0.25\ CH_2Cl_2$: C, 71.04; H, 6.48; N, 11.73; Found: C, 71.00; H, 6.49; N, 11.35.

Example 2
In Vitro Inhibition of Ras Farnesyl Transferase
Transferase Assays

Isoprenyl-protein transferase activity assays are carried out at 30° C. unless noted otherwise. A typical reaction contains (in a final volume of 50 μL): [$^3$H]farnesyl diphosphate, Ras protein, 50 mM HEPES, pH 7.5, 5 mM $MgCl_2$, 5 mM dithiothreitol, 10 μM $ZnCl_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801 scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor $IC_{50}$ determinations are as follows: FTase, 650 nM Ras-CVLS (SEQ.ID.NO.: 1), 100 nM farnesyl diphosphate.

The compounds of the instant invention described in the above Example 1 was tested for inhibitory activity against human FPTase by the assay described above and was found to have an $IC_{50}$ of ≦10 μM.

Example 3
Modified In Vitro GGTase Inhibition Assay

The modified geranylgeranyl-protein transferase inhibition assay is carried out at room temperature. A typical reaction contains (in a final volume of 50 μL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 μM $ZnCl_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ. ID.NO.: 2). Reactions are initiated by the addition of GGTase and stopped at timed intervals (typically 15 min) by the addition of 200 μL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and substrate concentrations for inhibitor $IC_{50}$ determinations are as follows: 75 pM GGTase-I, 1.6 μM Ras peptide, 100 nM geranylgeranyl diphosphate.

Example 4
Cell-based In Vitro Ras Farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al, J. *Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 5
Cell-based In Vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of compounds for Ras-induced cell transformation.

Rat 1 cells transformed with either v-ras, v-raf, or v-mos are seeded at a density of $1\times10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 6
Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid, pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(−)/SEAP.

The plasmid pDSE101 was constructed as follows: A restriction fragment containing part of the SEAP gene coding sequence was cut out of the plasmid pGEM7zf(−)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(−)/SEAP was constructed as follows. The SEAP gene was PCRed, in two segments from a human placenta cDNA library (Clontech) using the following oligos.

Sense strand N-terminal SEAP:

5'GAGAGGGAATTCGGGCCCTTCCTGCAT-
GCTGCTGCTGCTGCTGCTGGGC 3' (SEQ.ID.NO.:3)

Antisense strand N-terminal SEAP:

5'GAGAGAGCTCGAGGTTAACCCGGGT-
GCGCGGCGTCGGTGGT 3' (SEQ.ID.NO.:4)

Sense strand C-terminal SEAP:

5'GAGAGAGTCTAGAGTTAACCCGTGGTC-
CCCGCGTTGCTTCCT 3' (SEQ.ID.NO.:5)

Antisense strand C-terminal SEAP:

5'GAAGAGGAAGCTTGGTACCGC-
CACTGGGCTGTAGGTGGTGGCT 3' (SEQ.ID.NO.:6)

The N-terminal oligos (SEQ.ID.NO.: 4 and SEQ.ID.NO.: 5) were used to generate a 1560 bp N-terminal PCR product that contained EcoRI and HpaI restriction sites at the ends. The Antisense N-terminal oligo (SEQ.ID.NO.: 4) introduces an internal translation STOP codon within the SEAP gene along with the HpaI site. The C-terminal oligos (SEQ.ID.NO.: 5 and SEQ.ID.NO.: 6) were used to amplify a 412 bp C-terminal PCR product containing HpaI and HindIII restriction sites. The sense strand C-terminal oligo (SEQ.ID.NO.: 5) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electro-phoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang et al, 1987) containing the CMV immediate early promoter was cut with EcoRI generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc.Acids Res. 19, 3979–3986) to remove a SacI restriction site using site directed mutagenesis. The mutated intron A sequence was PCRed from the plasmid p16T-287 using the following oligos.

Sense strand:

5'GGCAGAGCTCGTTTAGTGAACCGTCAG 3' (SEQ.ID.NO.: 7)

Antisense strand:

5'GAGAGATCTCAAGGACGGTGACTGCAG 3' (SEQ.ID.NO.: 8)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP, contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Cloning of a Myristylated Viral-H-ras Expression Plasmid

A DNA fragment containing viral-H-ras can be PCRed from plasmid "H-1" (Ellis R. et al. J. Virol. 36, 408, 1980) or "HB-11 (deposited in the ATCC under Budapest Treaty on Aug. 27, 1997, and designated ATCC 209,218) using the following oligos.

Sense strand:

5'TCTCCTCGAGGCCACCATGGGGAGTAGCAAGAGCAAGCC
TAAGGACCCCAGCCAGCGCCGGATGACAGAATACAAGC
TTGTGGTGG 3'. (SEQ.ID.NO.: 9)

Antisense:

5'CACATCTAGATCAGGACAGCACAGACTTGC
AGC 3'. (SEQ.ID.NO.: 10)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site.

To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3'end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al., J. Virol. 36, 408, 1980) or "HB-11 (deposited in the ATCC under Budapest Treaty on Aug. 27, 1997, and designated ATCC 209,218) by PCR using the following oligos.

Sense strand:

5'TCTCCTCGAGGCCACCATGACAGAATACAAGCTTG
TGGTGG-3' (SEQ.ID.NO.: 11)

Antisense strand:

5'CACTCTAGACTGGTGTCAGAGCAGCACACACTTGCAGC-
3' (SEQ.ID.NO.: 12)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense strand:

5'-GAGAGAATTCGCCACCATGACGGAATATAAGCTGGTGG-
3' (SEQ.ID.NO.: 13)

Antisense strand:

5'-GAGAGTCGACGCGTCAGGAGAGCACACACT
TGC-3' (SEQ.ID.NO.: 14)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 15)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense strand:

5'-GAGAGAATTCGCCACCATGACTGAGTACAAACTGGTGG-3'  (SEQ.ID.NO.: 16)

Antisense strand:

5'-GAGAGTCGACTTGTTACATCACCACACAT GGC-3'  (SEQ.ID.NO.: 17)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3'  (SEQ.ID.NO.: 18)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense strand:

5'-GAGAGGTACCGCCACCATGACTGAATATAAACTTGTGG-3'  (SEQ.ID.NO.: 19)

Antisense strand:

5'-CTCTGTCGACGTATTTACATAATTACACACTTT GTC-3'  (SEQ.ID.NO.: 20)

The primers will amplify a c-K-ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K-ras fragment can be ligated into a KpnI-Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3'  (SEQ.ID.NO.: 21)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 µl of $CaCl_2$-DNA solution is added dropwise while vortexing to 600 µl of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+1×(Pen/Strep, Glutamine and NEAA). Transfected cells are plated in a 96 well microtiter plate (100 µl /well) to which drug, diluted in media, has already been added in a volume of 100 µl. The final volume per well is 200 µl with each drug concentration repeated in triplicate over a range of half-log steps.

Incubation of cells and test compound is for 36 hrs at 37° under $CO_2$. At the end of the incubation period, cells are examined microscopically for evidence of cell distress. Next, 100 µl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 µl media is combined with 200 µl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

DNA-$CaPO_4$ Precipitate for 10 cm. Plate of Cells

| | |
|---|---|
| Ras expression plasmid (1µg/µl) | 10 µl |
| DSE-SEAP Plasmid (1µg/µl) | 2 µl |
| Sheared Calf Thymus DNA (1µg/µl) | 8 µl |
| 2M $CaCl_2$ | 74 µl |
| $dH_2O$ | 506 µl |

2×HBS Buffer
280 mM NaCl
10 mM KCl
1.5 mM $Na_2HPO_4$ $2H_2O$
12 mM dextrose
50 mM HEPES
Final pH=7.05
Luminesence Buffer (26 ml)

| | |
|---|---|
| Assay Buffer | 20 ml |
| Emerald Reagent™(Tropix) | 2.5 ml |
| 100mM homoarginine | 2.5 ml |
| CSPD Reagent®(Tropix) | 1.0 ml |

Assay Buffer
Add 0.05M $Na_2CO_3$ to 0.05M $NaHCO_3$ to obtain pH 9.5. Make 1 mM in $MgCl_2$ Example 7

The processing assays employed in this example and in Example 8 are modifications of that described by DeClue et al [Cancer Research 51, 712–717, 1991].

K4B-Ras Processing Inhibition Assay

PSN-1 (human pancreatic carcinoma) cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000×concentrated solutions in DMSO to yield a final solvent concentration of 0.1%. Following incubation at 37° C. for two hours 204 $\mu$Ci/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 $\mu$g/ml AEBSF, 10 $\mu$g/ml aprotinin, 2 $\mu$g/ml leupeptin and 2 $\mu$g/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 $\mu$g of the pan Ras monoclonal antibody, Y13-259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 $\mu$l elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 $\mu$g Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleasesis added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to HDJ-2 (Neomarkers Cat. #MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of HDJ (the slower-migrating species) is calculated by densitometry. Dose-response curves and $IC_{50}$ values are generated using 4-parameter curve fits in SigmaPlot software.

Example 8

K4B-Ras Processing Inhibition Assay

PSN-1 (human pancreatic carcinoma) cells are used for analysis of protein processing. Subconfluent cells in 150 mm dishes are fed with 20 ml of media (RPMI supplemented with 15% fetal bovine serum) containing the desired concentration of prenyl-protein transferase inhibitor or solvent alone. Cells treated with lovastatin (5–10 $\mu$M), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%.

The cells are incubated at 37° C. for 24 hours, the media is then removed and the cells are washed twice with cold PBS. The cells are scraped into 2 ml of cold PBS, collected by centrifugation (10,000×g for 5 min at 4° C.) and frozen at –70° C. Cells are lysed by thawing and addition of lysis buffer (50 mM HEPES, pH 7.2, 50 mM NaCl, 1% CHAPS, 0.7 $\mu$g/ml aprotinin, 0.7 $\mu$g/ml leupeptin 300 $\mu$g/ml pefabloc, and 0.3 mM EDTA). The lysate is then centrifuged at 100,000×g for 60 min at 4° C. and the supernatant saved. The supernatant may be subjected to SDS-PAGE, HPLC analysis, and/or chemical cleavage techniques.

The lysate is applied to a HiTrap-SP (Pharmacia Biotech) column in buffer A (50 mM HEPES pH 7.2) and resolved by gradient in buffer A plus 1 M NaCl. Peak fractions containing Ki4B-Ras are pooled, diluted with an equal volume of water and immunoprecipitated with the pan Ras monoclonal antibody, Y13-259 linked to agarose. The protein/antibody mixture is incubated at 4° C. for 12 hours. The immune complex is washed 3 times with PBS, followed by 3 times with water. The Ras is eluted from the beads by either high pH conditions (pH>10) or by heating at 95° C. for 5 minutes, after which the beads are pelleted by brief centrifugation. The supernatant may be subjected to SDS-PAGE, HPLC analysis, and/or chemical cleavage techniques.

Example 9

Rap1 Processing Inhibition Assay

Protocol A

Cells are labeled, incubated and lysed as described in Example 7.

For immunoprecipitation of Rap1, samples of lysate supernatant containing equal amounts of protein are utilized.

Protein concentration is determined by the bradford method utilizing bovine serum albumin as a standard. The appropriate volume of lysate is brought to 1 ml with lysis buffer lacking DTT and 2 µg of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 µl elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 µg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer acking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B

PSN-1 cells are passaged every 3–4 days in 10 cm plates, splitting near-confluent plates 1:20 and 1:40. The day before the assay is set up, $5 \times 10^6$ cells are plated on 15 cm plates to ensure the same stage of confluency in each assay. The media for these cells is RPM1 1640 (Gibco), with 15% fetal bovine serum and 1×Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in ½-log dilutions. The range of final concentrations to be assayed is generally 0.1–100 µM. Four concentrations per compound is typical. The compounds are diluted so that each concentration is 1000×of the final concentration (i.e., for a 10 µM data point, a 10 mM stock of the compound is needed).

2 µL of each 1000×compound stock is diluted into 1 ml media to produce a 2×stock of compound. A vehicle control solution (2 µL DMSO to 1 ml media), is utilized. 0.5 ml of the 2×stocks of compound are added to the cells.

After 24 hours, the media is aspirated from the assay plates. Each well is rinsed with 1 ml PBS, and the PBS is aspirated. 180 µL SDS-PAGE sample buffer (Novex) containing 5% 2-mercaptoethanol is added to each well. The plates are heated to 100° C. for 5 minutes using a heat block containing an adapter for assay plates. The plates are placed on ice. After 10 minutes, 20 µL of an RNAse/DNase mix is added per well. This mix is 1 mg/ml DNaseI (Worthington Enzymes), 0.25 mg/ml Rnase A (Worthington Enzymes), 0.5M Tris-HCl pH8.0 and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 µl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30 V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rapla antibody (Santa Cruz Biochemical SC 1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rapla Minimum Inhibitory Concentration is determined from the lowest concentration of compound that produces a detectable Rapla Western signal. The Rap1a antibody used recognizes only unprenylated/unprocessed Rap1a, so that the precence of a detectable Rap1a Western signal is indicative of inhibition of Rap1a prenylation.

Example 10

In Vivo Tumor Growth Inhibition Assay (Nude Mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle or compound treatment group. Animals are dosed subcutaneously starting on day 1 and daily for the duration of the experiment. Alternatively, the prenyl-protein transferase inhibitor may be administered by a continuous infusion pump. Compound or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound as illustrated by formula F:

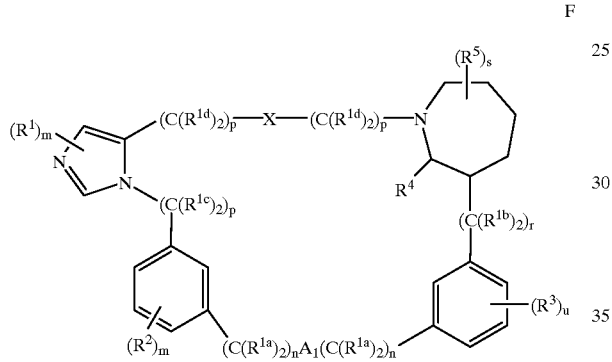

wherein:

$R^{1a}$, $R^{1b}$, $R^{1c}$ and $R^{1d}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $NO_2$, $R^8C(O)$—, $R^8OC(O)$—, $N(R^8)_2$, $(R^8)_2NC(O)$—, $C(O)N(R^8)_2$—, or $N_3$;
  c) $C_1$–$C_6$ alkyl, unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_q$—, CN, $R^8C(O)$—, $R^8OC(O)$—, $N(R^8)_2$, $N_3$, or $R^8C(O)O$—;

$R^1$ is selected from:
  a) H,
  b) unsubstituted or substituted $C_1$–$C_6$ alkyl,
  c) unsubstituted or substituted aryl,
  d) unsubstituted or substituted heterocycle,
  e) —($C_1$–$C_6$ alkyl)$N(R^8)_2$,
  f) —$R^8C(O)R^8$,
  g) —($C_1$–$C_6$ alkyl)$OR^8$,
  h) —$N(R^8)_2$,
  i) —$OR^8$,
  j) —$R^8NHC(O)R^8$,
  k) —$R^8C(O)N(R^8)_2$,
  l) $CF_3$,
  m) halo,
  n) —$C(O)OR^8$,
  o) $C_2$–$C_6$ alkynyl,
  p) $C_2$–$C_6$ alkenyl,
  q) perfluoroalkyl,
  r) $N_3$,
  s) $NO_2$,
  t) CN, and
  u) $R^9S(O)_q$—

$R^2$ is selected from:
  a) hydrogen,
  b) CN,
  c) $NO_2$,
  d) halogen,
  e) aryl, unsubstituted or substituted,
  f) heteroaryl, unsubstituted or substituted,
  g) $C_1$–$C_6$ alkyl, unsubstituted or substituted,
  h) $OR^8$,
  i) $N_3$,
  j) $R^9S(O)_q$,
  k) $R^8HC=CH$—, and
  l) $R^8C\equiv C$—;

$R^3$ is selected from:
  a) H,
  b) CN,
  c) $NO_2$,
  d) halogen,
  e) $C_1$–$C_6$ alkyl, unsubstituted or substituted,
  f) $OR^8$,
  g) aryl, unsubstituted or substituted,
  h) heteroaryl, unsubstituted or substituted, and
  i) $CF_3$;

$R^4$ is H;

$R^5$ is selected from:
  a) H,
  b) CN,
  c) $NO_2$,
  d) halogen,
  e) $C_1$–$C_6$ alkyl, unsubstituted or substituted,
  f) $N_3$,
  g) $R^9S(O)_q$,
  h) —$HC=CH_2$,
  i) $HC\equiv C$—,
  j) aryl, unsubstituted or substituted,
  k) heterocycle, unsubstituted or substituted,
  l) $CF_3O$—,
  m) $CF_3CH_2O$—,
  n) $C_3$–$C_{10}$ cycloalkyl,
  o) $CF_3$,
  p) —($C_1$–$C_6$ alkyl)$N(R^8)_2$, q) —(C$_1$–C$_6$ alkyl)OR$^8$,
r) OR$^8$,
s) N(R$^8$)$_2$,
t) —C(O)(C$_1$–C$_6$ alkyl), and
u) —(C$_1$–C$_6$ alkyl)C(O)R$^8$;

R$^8$ is independently selected from hydrogen, unsubstituted or substituted C$_1$–C$_6$ alkyl, unsubstituted or substituted benzyl, unsubstituted or substituted heterocycle and unsubstituted or substituted aryl;

R$^9$ is independently selected from unsubstituted or substituted C$_1$–C$_6$ alkyl, unsubstituted or substituted benzyl and unsubstituted or substituted aryl;

A$^1$ is selected from:
  a) a bond, or
  b) O;

X is selected from: a bond or —C(=O)—;
Z is an aryl;
m is 0, 1, 2, 3 or 4;
n is 0, 1, 2, 3 or 4;
p is 0, 1, 2, 3 or 4;
q is 0, 1 or 2;
r is 0, 1, 2, 3, or 4;
s is 0, 1, 2, 3 or 4;
u is 0, 1, 2, 3 or 4;

or a pharmaceutically acceptable salt or stereoisomer thereof.

2. A compound as illustrated by formula G:

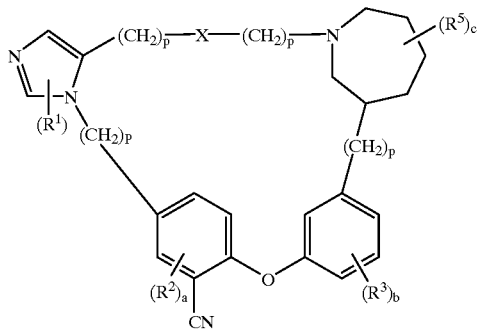

wherein:
R$^1$ is selected from:
  a) H,
  b) unsubstituted or substituted C$_1$–C$_6$ alkyl,
  c) unsubstituted or substituted aryl,
  d) unsubstituted or substituted heterocycle,
  e) —(C$_1$–C$_6$ alkyl)N(R$^8$)$_2$,
  f) —R$^8$C(O)R$^8$,
  g) —(C$_1$–C$_6$ alkyl)OR$^8$,
  h) —N(R$^8$)$_2$,
  i) —OR$^8$,
  j) —R$^8$NHC(O)R$^8$,
  k) —R$^8$C(O)N(R$^8$)$_2$,
  l) CF$_3$,
  m) halo,
  n) —C(O)OR$^8$,
  o) C$_2$–C$_6$ alkynyl,
  p) C$_2$–C$_6$ alkenyl,
  q) perfluoroalkyl,
  r) N$_3$,
  s) NO$_2$,
  t) CN, and
  u) R$^9$S(O)$_q$—

R$^2$ is selected from:
  a) hydrogen,
  b) CN,
  c) NO$_2$,
  d) halogen,
  e) aryl, unsubstituted or substituted,
  f) heteroaryl, unsubstituted or substituted,
  g) C$_1$–C$_6$ alkyl, unsubstituted or substituted,
  h) OR$^8$,
  i) N$_3$,
  j) R$^9$S(O)$_q$,
  k) R$^8$HC=CH—, and
  l) R$^8$C≡C—;

R$^3$ is selected from:
  a) H,
  b) CN,
  c) NO$_2$,
  d) halogen,
  e) C$_1$–C$_6$ alkyl, unsubstituted or substituted,
  f) OR$^8$,
  g) aryl, unsubstituted or substituted,
  h) heteroaryl, unsubstituted or substituted, and
  i) CF$_3$;

R$^5$ is selected from:
  a) H,
  b) CN,
  c) NO$_2$,
  d) halogen,
  e) C$_1$–C$_6$ alkyl, unsubstituted or substituted,
  f) N$_3$,
  g) R$^9$S(O)$_q$,
  h) —HC=CH$_2$,
  i) HC≡C—,
  j) aryl, unsubstituted or substituted,
  k) heterocycle, unsubstituted or substituted,
  l) CF$_3$O—,
  m) CF$_3$CH$_2$O—,
  n) C$_3$–C$_{10}$ cycloalkyl,
  o) CF$_3$,
  p) —(C$_1$–C$_6$ alkyl)N(R$^8$)$_2$,
  q) —(C$_1$–C$_6$ alkyl)OR$^8$,
  r) OR$^8$,
  s) N(R$^8$)$_2$,
  t) —C(O)(C$_1$–C$_6$ alkyl), and
  u) —(C$_1$–C$_6$ alkyl)C(O)R$^8$;

X is selected from: a bond or —C(=O)—;
a is 0, 1 or 2;
b is 0, 1 or 2;
c is 0, 1, 2 or 3;
p is 0, 1, 2 or 3;

or a pharmaceutically acceptable salt or sterioisomer thereof.

3. A compound of the structural formula:

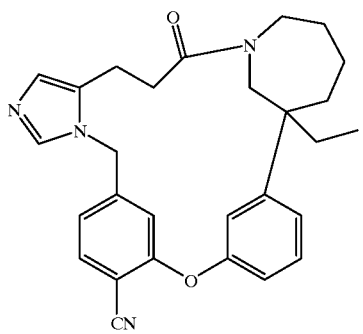

(±) 5H-17-Ethyl-17,22-methano-18,19,20,21,23,24-hexahydro-23-oxo-6,10:12,16-dimetheno-25H-imidazo[3,4-h]-[1,11,16]oxadiazacyclodocosane-9-carbonitrile or a pharmaceutically acceptable salt, an optical isomer or stereoisomer thereof.

4. A pharmaceutical composition comprising a pharmaceutical carrier and a therapeutically effective amount of a compound of claim 1.

5. A pharmaceutical composition comprising a pharmaceutical carrier, and dispersed therein, a therapeutically effective amount of a compound of claim 3.

6. A method for treating ras-dependent cancer which comprises administering to a mammal in need thereof a therapeutically effective amount of a composition of claim 4.

7. A method for treating ras-dependent cancer which comprises administering to a mammal in need thereof a therapeutically effective amount of a composition of claim 5.

8. A method for treating neurofibromin benign proliferative disorder which comprises administering to a mammal in need thereof a therapeutically effective amount of a composition of claim 4.

9. A method for treating blindness related to retinal vascularization which comprises administering to a mammal in need thereof a therapeutically effective amount of a composition of claim 4.

10. A method for treating infections from hepatitis delta and which comprises administering to a mammal in need thereof a therapeutically effective amount of a composition of claim 4.

11. A method for preventing restenosis which comprises administering to a mammal in need thereof a therapeutically effective amount of a composition of claim 4.

12. A method for treating polycystic kidney disease which comprises administering to a mammal in need thereof a therapeutically effective amount of a composition of claim 4.

13. A pharmaceutical composition made by combining the compound of claim 1 and a pharmaceutically acceptable carrier.

14. A process for making a pharmaceutical composition comprising combining a compound of claim 1 and a pharmaceutically acceptable carrier.

15. A method of conferring radiation sensitivity on a ras dependent tumor cell comprising administering to a mammal in need thereof a therapeutically effective amount of a composition of claim 4 in combination with radiation therapy.

16. A method of treating a ras dependent cancer comprising administering to a mammal in need thereof a therapeutically effective amount of a composition of claim 4 in combination with an antineoplastic.

17. A method according to claim 16 wherein the antineoplastic is paclitaxel.

* * * * *